United States Patent
Rigaut et al.

(10) Patent No.: US 11,554,170 B2
(45) Date of Patent: Jan. 17, 2023

(54) IMMUNOGENIC FORMULATIONS COMPRISING LINEAR OR BRANCHED POLYACRYLIC ACID POLYMER ADJUVANTS

(71) Applicants: BOEHRINGER INGELHEIM ANIMAL HEALTH USA INC., Duluth, GA (US); SANOFI PASTEUR, Duluth, GA (US)

(72) Inventors: Guillaume Rigaut, Lyons (FR); Alexis Guy André Lucien Parisot, Lyons (FR); Karelle De Luca, Villette De Vienne (FR); Christine Michele Pierrette Andreoni, Villette D'Anthon (FR); Lydie Remolue, Lyons (FR); Marie Garinot, Lyons (FR); Jean-François Cotte, Lozanne (FR); Patricia Probeck-Quellec, Lyons (FR); Jean Haensler, Grezieu la Varenne (FR); Véronique Chambon, Curis-Au-Mont-D'Or (FR); Philippe Talaga, Sainte Consorce (FR)

(73) Assignees: Sanofi Pasteur SA, Lyons (FR); Boehringer Ingelheim Animal Health USA Inc., Duluth, GA (US)

( * ) Notice: Subject to any disclaimer, the term of this patent is extended or adjusted under 35 U.S.C. 154(b) by 0 days.

(21) Appl. No.: 15/624,405

(22) Filed: Jun. 15, 2017

(65) Prior Publication Data

US 2017/0360923 A1 Dec. 21, 2017

Related U.S. Application Data

(60) Provisional application No. 62/351,492, filed on Jun. 17, 2016.

(51) Int. Cl.
| | | |
|---|---|---|
| A61K 39/39 | (2006.01) | |
| C08F 120/06 | (2006.01) | |
| A61K 39/00 | (2006.01) | |
| A61K 47/08 | (2006.01) | |
| A61K 47/26 | (2006.01) | |

(52) U.S. Cl.
CPC ............ *A61K 39/39* (2013.01); *A61K 39/00* (2013.01); *A61K 39/0011* (2013.01); *A61K 47/08* (2013.01); *A61K 47/26* (2013.01); *A61K 2039/555* (2013.01); *A61K 2039/55511* (2013.01); *A61K 2039/55516* (2013.01); *A61K 2039/55522* (2013.01); *A61K 2039/55555* (2013.01); *A61K 2039/55561* (2013.01); *A61K 2039/57* (2013.01); *A61K 2300/00* (2013.01); *C08F 120/06* (2013.01); *Y02A 50/30* (2018.01)

(58) Field of Classification Search
CPC .................. A61K 39/39; A61K 8/8147; A61K 2039/555; C08F 120/06

See application file for complete search history.

(56) References Cited

U.S. PATENT DOCUMENTS

| | | |
|---|---|---|
| 3,790,665 A | 2/1974 | Glass et al. |
| 3,919,411 A | 11/1975 | Glass et al. |
| 4,705,683 A | 11/1987 | Dettmar |
| 6,340,464 B1 | 1/2002 | Hilgers et al. |
| 6,610,310 B2 | 8/2003 | Hilgers |
| 7,163,926 B1 | 1/2007 | Merial |
| 2006/0057163 A1 | 3/2006 | Merial |
| 2009/0176866 A1 | 7/2009 | Shaunak et al. |
| 2015/0044242 A1 | 2/2015 | Gerber et al. |

FOREIGN PATENT DOCUMENTS

| | | |
|---|---|---|
| JP | S61-205213 A | 9/1986 |
| WO | WO1998017310 | 4/1998 |
| WO | WO 2009/118523 A1 | 10/2009 |
| WO | WO2011100665 | 8/2011 |

OTHER PUBLICATIONS

Ji et al., Journal of Macromolecular Science, Part A: Pure and Applied Chemistry (2010) 47, 445-451.*
Remington, The Science and Practice of Pharmacy, Nineteenth Edition-1995, pp. 1463, 1546-1547.*
Ahmad Fuaad. PhD Submission. University of Queensland, Australia. "The development of peptide-based subunit vaccines against *Streptococcus pyogenes*, Necator americanus and Schistosome mansoni." Published May 28, 2015.
Hilgers, L. et al. "Alkyl-esters of polyacrylic acid as vaccine adjuvants." Vaccine, vol. 16, No. 16, pp. 1575-1581, 1998.
Hilgers, L. et al. "Alkyl-Polyacrylate Esters are Strong Mucosal Adjuvants." Vaccine, 2000, 18, 3319-3325.
Topuzogullari, M. et al. "Molecular-weightdistribution and structural transformation in water-soluble complexes of poly(acrylic acid) and bovine serum albumin." European Polymer Journal 43 (2007) 2935-2946.
Vialle et al. "Microgel particulate adjuvant: characterisation and mechanisms of action." Procedia in Vaccinology 2 (2010) 12-16.
Office Action for Korean Application No. KR 10-2019-7001525, dated Feb. 28, 2022. 16 pages.

(Continued)

*Primary Examiner* — Shobha Kantamneni
(74) *Attorney, Agent, or Firm* — Wolf, Greenfield & Sacks, P.C.

(57) ABSTRACT

The present invention provides for novel immunological and vaccine formulations comprising a newly applied non-cross-linked polyacrylic acid polymer adjuvant. The adjuvants may be combined with a wide variety of immunogens to produce vaccines that are safe and effective when administered to a wide range of target animals. The immunogens may include, but are not limited to: inactivated pathogens, attenuated pathogens, subunits, recombinant expression vectors, plasmids or combinations thereof. The animals may include, but are not limited to: humans, murine, canines, felines, equines, porcines, ovines, caprines and bovines.

16 Claims, 9 Drawing Sheets

(56) References Cited

OTHER PUBLICATIONS

Hilgers et al., Effect of various adjuvants on secondary immune response in chickens. Vet Immunol Immunopathol. Nov. 24, 1998;66(2):159-71. doi: 10.1016/s0165-2427(98)00188-3.

[No. Author Listed], Material Safety Data Sheet for Poly(Acrylic Acid) Sodium Salt MW 225 000 20% Solids in Water. Issued Nov. 15, 2013. 5 pages.

Moad et al., End-functional polymers, thiocarbonylthio group removal/transformation and reversible addition-fragmentation-chain transfer (RAFT) polymerization. Polym Int. 2011;60:9-25.

Veloso et al., Determining the effect of side reactions on product distributions in RAFT polymerization by MALDI-TOF MS. Polym Chem. 2015;6:5437-5450.

* cited by examiner

FIG. 10

IMMUNOGENIC FORMULATIONS COMPRISING LINEAR OR BRANCHED POLYACRYLIC ACID POLYMER ADJUVANTS

CROSS-REFERENCE TO RELATED APPLICATIONS

This application claims priority to U.S. provisional application No. 62/351,492, filed 17 Jun. 2016, and incorporated herein by reference in its entirety.

INCORPORATION BY REFERENCE

Any foregoing applications and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. Citation or identification of any such document in this application is not an admission that such document is available as prior art to the present invention and does not reflect any view of the validity, patentability and/or enforceability of such cited patent documents. All sequences referenced herein by Gen-Bank Accession numbers are herein incorporated by reference in their entirety, and said sequences are as set forth in GenBank at as of the filing date of the present application.

FIELD OF THE INVENTION

This invention belongs to the field of vaccines. In particular, the invention is related to particular adjuvants and adjuvanted compositions and to processes for preparing such adjuvants and adjuvanted compositions.

BACKGROUND OF THE INVENTION

The use of polymers including acrylic acid units as an adjuvant in vaccine composition has already been proposed. In most cases, polyacrylic acid polymers recommended as an adjuvant are cross-linked polymers. For instance, U.S. Pat. Nos. 3,790,665 and 3,919,411 describe the use of an acrylic acid polymer cross-linked with a polyallyl saccharide, as an adjuvant. Adjuvants corresponding to polymers of acrylic or methacrylic acid which are cross-linked, especially with polyalkenyl ethers of sugars or polyalcohols, are also described in U.S. Pat. No. 7,163,926. Such kinds of polymers are sold under the name CARBOPOL®. The use of CARBOPOL 974P, 934P and 971P which are cross-linked polymers with high Mw (i.e. about 3 million for 974P, according to the data provided by the producer) is described in U.S. Pat. No. 7,163,926, EP 1 058 558 and WO 2009/118523.

Some research efforts have focused on the use of linear polyacrylic acid polymers which have a low weight or on acrylic acid/acrylic acid ester copolymers:

WO 2005/065712 proposes a complex that comprises a narrow molecular weight distribution polymer that includes units derived from an acrylic acid or a salt thereof, and a substance that has a pharmacological activity against a pathogenic organism or a cancer, or one or more antigens or immunogens. The polymer may be a homopolymer or a copolymer of an acrylic acid or methacrylic acid or a salt thereof. A molecular weight of 100 000 or less is advocated.

U.S. Pat. No. 6,610,310 and EP 0 804 234 describe the use of a polymer having anionic constitutive repeating monomer units and hydrophobic constitutive repeating monomer units. In particular, EP0804234 discloses the use of a polymer partially consisting of acrylic acid units (constitutive repeating units anionic) and ester of acrylic acid units (constitutive hydrophobic repeating units) as a vaccine adjuvant in an aqueous solution. A polyacrylic acid polymer CARBOPOL® 907 is compared in these documents to its advocated homologous partially esterified polyacrylic acid polymers and provides a poorer immune response. Similarly, the publications of L. Hilgers et al. in Vaccine, 2000, 18, 3319-3325 and Vaccine 1998 Vol. 16, No. 16, 1575-1581 also disclose the use of such esterified polymers and teach that the use of alkyl esters of polyacrylic acid provides a better immune response in the majority of the cases. CARBOPOL® 907 is a polyacrylic acid polymer that is not available today anymore and whose characteristics cannot be reliably determined. It belongs to the CARBOPOL family which is known as cross-linked polymers. This polymer has a weight average molecular weight Mw which is different from a document to another one: the publication of Vaccine, 1998 Vol. 16, No. 16, page 1575 to 1581 provides a weight average molecular weight Mw of 450 kDa without precision regarding the method used for its determination. It does not mention its polydispersity index. In contrast, "Liquid Detergents", surfactant series Science, Vol. 67, page 147 (1996, CRC Press, Publisher: Kuo-Yann Lai), provided for the same polymer a weight average molecular weight Mw of 603.3 kDa determined by chromatographic technique by gel permeation (GPC) and a polydispersity index IP of 4.124. There is doubt regarding the characteristics of CARBOPOL® 907. Additionally, most of the time, the Mw data given by the producers differ from the Mw that can be determined by standardized methods, as shown in the examples of the present patent application.

In addition to the uncertainties as to the precise characteristics of existing polymer adjuvants, there is an ongoing need to develop new adjuvants with improved safety and efficacy properties. The instant disclosure fills those needs by providing safe and effective immunological and vaccine formulations comprising non-crosslinked acrylic acid polymer adjuvants.

BRIEF SUMMARY OF THE INVENTION

In a first aspect, the disclosure provides formulations comprising a new class of polymers as a vaccine adjuvant. As disclosed herein, this class of polymers has demonstrated safety and efficacy in adjuvanting formulations across a wide variety of antigens, for use in administration of a wide variety of animal species. This class of polymers produces advantageous adjuvant properties, in comparison with other families of polyacrylic acid polymers used in the prior art.

In an embodiment of the first aspect, the invention provides a family of polymers that is particularly effective as an adjuvant. In a particular embodiment, the invention provides a class of polymers that unexpectedly promotes strong Th-1 responses, in addition to Th-2 responses.

Additionally, some polymers selected according to the invention lead to an adjuvant composition and, as a result to a vaccine composition. In a particular embodiment, the vaccine compositions of the instant disclosure are safer, particularly as to reproducibility and reduction of contaminants, which are often incompatible with vaccine storage stability. In a more particular embodiment, the selected polymers are also stable and sterilizable by autoclaving.

In this context, the invention concerns a pharmaceutically acceptable salt of a linear or branched polyacrylic acid polymer, for its use as an adjuvant in a vaccine composition, characterized in that said polyacrylic acid polymer salt has a weight average molecular weight Mw in the range of 350 to 650 kDa.

In particular, said polyacrylic acid polymer salt is exclusively composed of units corresponding to a salt of acrylic acid or is exclusively composed of units corresponding to the free acid form of acrylic acid and of units corresponding to a salt of acrylic acid.

Advantageously, said polyacrylic acid polymer salt comprises less than 0.005%, preferably less than 0.001%, w/w of oxidizing agents, based on the total dry weight of said polyacrylic acid polymer salt and/or comprises less than 0.005%, preferably less than 0.001%, w/w of persulfates, based on the total dry weight of said polyacrylic acid polymer salt.

In a more particular embodiment, said polyacrylic acid polymer is a salt with $Na^+$.

In particular embodiments, said polyacrylic acid polymer salt has a polydispersity index below or equal to about 4, preferably below or equal to about 2.5.

In particular embodiments, said polyacrylic acid polymer salt has a weight average molecular weight Mw in the range of 380 to 620 kDa and a polydispersity index below or equal to 4; or has a weight average molecular weight Mw in the range of 400 to 600 kDa and a polydispersity index below or equal to 4; or has a weight average molecular weight Mw in the range of 380 to 620 kDa and a polydispersity index below or equal to 2.5; or has a weight average molecular weight Mw in the range of 400 to 600 kDa and a polydispersity index below or equal to 2.

Advantageously, said polyacrylic acid polymer salt comprises less than 0.005% w/w of acrylic acid monomer in free acid form or salt form, based on the total dry weight of said polyacrylic acid polymer salt.

According to advantageous embodiments, said polyacrylic acid polymer salt is diafiltered and sterilized.

Advantageously, the polyacrylic acid polymer salt described in the invention is used for enhancing the Th1 immune response obtained with the vaccine composition. The Th1 immune response is higher than the Th1 immune response obtained when polyacrylic acid polymer salt of lower molecular weight Mw are used, as adjuvant.

Another aspect of the invention also concerns a process for the preparation of a pharmaceutically acceptable salt of a polyacrylic acid polymer described in the invention comprising the following successive steps:

a) having a solution of a polyacrylic acid polymer,
b) purifying the solution of the polyacrylic acid polymer, in order to eliminate impurities, and
c) sterilizing the purified solution of the polyacrylic acid polymer.

The invention also concerns a process for the storage of a solution of the polyacrylic acid polymer salt described in the invention comprising such a preparation process, followed by a storage step of the obtained pharmaceutically acceptable salt of the polyacrylic acid polymer, in solution.

In a third aspect, the invention also concerns a vaccine composition comprising at least one vaccine agent (e.g. an immunogen or a nucleic acid encoding an immunogen) and a pharmaceutically acceptable salt of polyacrylic acid polymer described in the invention. In a particular embodiment, the immunogen may be selected from: inactivated pathogens, attenuated pathogens, sub-unit antigens, purified antigens, unpurified antigens, or antigens produced recombinantly using bacterial, yeast, plant, insect, or animal cells, expression vectors including plasmids, and the like. The antigens may be purified by means well-known in the art including, but not limited to, ultrafiltration, ultracentrifugation, size-exclusion gel-filtration, ion-exchange chromatography, and PEG-purification. The pathogen may be bacterial, viral, protozoal, or fungal in origin or the immunogen may constitute an antitoxin.

In yet another aspect, the present invention provides for a method of inducing an immune response in a vaccinate against a pathogen comprising administering the vaccine composition of the present invention to the vaccinate.

It is noted that in this disclosure and particularly in the claims, terms such as "comprises", "comprised", "comprising" and the like can have the meaning attributed to such terms in U.S. Patent law; e.g., they can mean "includes", "included", "including", and the like; and that terms such as "consisting essentially of" and "consists essentially of" have the meaning ascribed to them by U.S. Patent law, e.g., they allow for elements not explicitly recited, but exclude elements that are found in the prior art or that affect a basic or novel characteristic of the invention.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

These and other embodiments are disclosed or are obvious from and encompassed by, the following Detailed Description.

BRIEF DESCRIPTION OF DRAWINGS

A full and enabling disclosure of the present invention, including the best mode thereof, to one of ordinary skill in the art, is set forth more particularly in the remainder of the specification, including reference to the accompanying figures, wherein:

FIG. 10 is a graph presenting an expansion of the Day 41 serology data shown in FIG. 9;

DETAILED DESCRIPTION OF THE INVENTION

Figure 1:
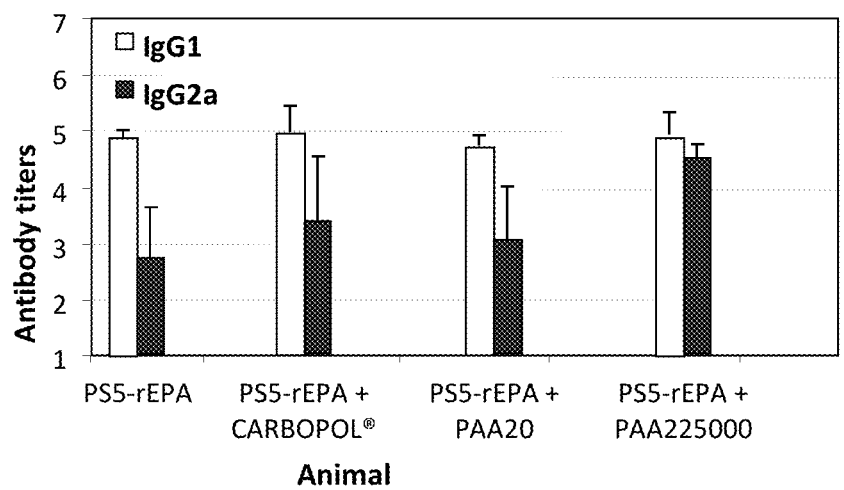
FIG. 1 is a graph showing antibody titers (IgG1 and IgG2a) for OF1 mice immunized on D0, D21 and D35 with 2.5 µg PS5-rEPA per mouse per injection, injected alone or co-injected with either 200 µg CARBOPOL, PAA20 or PAA225000.

Other objects, features and aspects of the present invention are disclosed in, or are obvious from, the following Detailed Description. It is to be understood by one of ordinary skill in the art that the present discussion is a description of exemplary embodiments only and is not intended as limiting the broader aspects of the present invention, which broader aspects are embodied in the exemplary construction. In fact, it will be apparent to those skilled in the art that various modifications and variations can be made in the present invention without departing from the scope or spirit of the invention. For instance, features illustrated or described as part of one embodiment can be used in another embodiment to yield a still further embodiment. It is intended that the present invention cover such modifications and variations as come within the scope of the appended claims and their equivalents. The contents of all references, published patents, and patents cited throughout the present application are hereby incorporated by reference in their entirety.

Features of the Polyacrylic Acid Polymer

The polymer used in the invention is a linear or a branched polyacrylic acid polymer, but it is not a cross-linked polymer. By "polyacrylic acid polymer", we mean a polymer which is exclusively composed of acrylic acid units. So, in the form of a salt, said polyacrylic acid polymer salt is exclusively composed of units corresponding to a salt of acrylic acid or is exclusively composed of units corresponding to the free acid form of acrylic acid and of units corresponding to a salt of acrylic acid.

A linear or a branched polyacrylic acid polymer is obtained by polymerization of only acrylic acid as monomer. The polymerization, is, most of the time, carried out by radical polymerization, using an oxidizing agent as initiator or catalyst. The most used oxidizing agents are persulfate (peroxydisulfate), for instance sodium or potassium persulfate. Branched polyacrylic acid polymers are, for instance, described in Macromolecules 2011, 44, 5928-5936. When the polymer according to the invention is linear, its Mark Houwink slope is higher or equal to 0.7 (Yan J. K., Pei J. J., Ma H. L., Wang Z. B. 2015. Effects of ultrasound on molecular properties, structure, chain conformation and degradation kinetics of carboxylic curdlan. Carb. Polymers. 121, 64-70).

By "pharmaceutically acceptable salt" of the polyacrylic acid polymer, we mean salt of anionic forms of the polymer with cation(s), in particular with monovalent cation(s), which is(are) pharmaceutically acceptable. Examples of monovalent cation are alkali metal cations, such as $Na^+$ or $K^+$, or ammonium cations such as $NH_4^+$. In an aqueous solution of a pH from 5.5 to 8, for instance close to 7, the acidic groups of the polyacrylic acid polymer will be in an anionic form, forming a salt with a cation which will also be present in the aqueous solution. In the polymer, we can have acrylic acid units with the acid group in the free acidic form and other units with the acid group in the anionic form forming a salt. Depending on the pH, the acid groups of the polymer may be exclusively in the free acid form or, in salt cases, the acid groups of the polymer may be exclusively in the salt form, or some acid groups may be in the acidic form and others in the salt form. The preferred salts of the polyacrylic acid polymers of the invention are salts with $Na^+$. So, whichever of the embodiment described in the invention, the polyacrylic acid polymer will preferably be in the form of a sodium salt and, in that case, all the characteristics (Mw, IP, monomer and persulfate contents . . . ) will concern the salt (i.e. the sodium salt) of the polyacrylic acid polymer.

In the specification of the present patent application, this "pharmaceutically acceptable salt of polyacrylic acid polymer" will simply be called the "polyacrylic acid polymer salt" and is preferably a polyacrylic acid polymer sodium salt.

The polyacrylic acid polymer salt can be in a solid form (precipitate or powder) or preferably in a liquid formulation. A liquid formulation will include the polyacrylic acid polymer salt and an aqueous solution. Preferably, such a formulation has a pH in the range of 5.5 to 8.0. This pH can be obtained by incorporation of a base, like NaOH, in the aqueous solution. The aqueous solution can be a buffered aqueous solution, obtained with a buffer such as a phosphate buffer, a TRIS (2-amino-2-hydroxymethyl-1,3-propanediol), Hepes (acide 4-(2-hydroxyethyl)-1-piperazine ethane sulfonique), histidine or citrate buffer. The liquid formulation may also comprise one or several additional salts, such as NaCl.

According to the invention, it is proposed to use as an adjuvant a polyacrylic acid polymer salt or a liquid formulation of a polyacrylic acid polymer salt having one of the following characteristics, any combination of such characteristics or even all the following characteristics if they do not exclude one another:

the polyacrylic acid polymer salt has a weight average molecular weight Mw in the range of 350 to 650 kDa;

the polyacrylic acid polymer salt or the liquid formulation of the polyacrylic acid polymer salt comprises less than 0.005%, preferably less than 0.001%, w/w of oxidizing agents, based on the total dry weight of said polyacrylic acid polymer salt and/or less than 0.005%, preferably less than 0.001%, w/w of persulfates, based on the total dry weight of said polyacrylic acid polymer salt;

the polyacrylic acid polymer salt has a polydispersity index below or equal to 4, preferably below or equal to 2.5;

the polyacrylic acid polymer salt has a weight average molecular weight Mw in the range of 380 to 620 kDa and a polydispersity index below or equal to 4 or has a weight average molecular weight Mw in the range of 400 to 600 kDa and a polydispersity index below or equal to 4;

the polyacrylic acid polymer salt has a weight average molecular weight Mw in the range of 380 to 620 kDa and a polydispersity index below or equal to 2.5 or has a weight average molecular weight Mw in the range of 400 to 600 kDa and a polydispersity index below or equal to 2;

the polyacrylic acid polymer salt has a Mark Houwink slope higher or equal to 0.7;

the polyacrylic acid polymer salt or the liquid formulation of the polyacrylic acid polymer salt comprises less than 0.005% w/w of acrylic acid monomer in free acid form or salt form, based on the total dry weight of said polyacrylic acid polymer salt.

In particular, it is proposed to use as an adjuvant a polyacrylic acid polymer salt or a liquid formulation of a polyacrylic acid polymer salt characterized by:

a weight average molecular weight Mw in the range of 380 to 620 kDa and a polydispersity index below or equal to 4, a content of persulfates in the polyacrylic acid polymer salt or in the liquid formulation of the polyacrylic acid polymer salt less than 0.005%, preferably less than 0.001%, w/w, based on the total dry weight of said polyacrylic acid polymer salt and a content of acrylic acid monomer in free acid form or salt form in the polyacrylic acid polymer salt or in the liquid formulation of the polyacrylic acid polymer salt less than 0.005% w/w, based on the total dry weight of said polyacrylic acid polymer salt; advantageously, this polyacrylic acid polymer salt has a Mark Houwink slope higher or equal to 0.7, or a weight average molecular weight Mw in the range of 380 to 620 kDa and a polydispersity index below or equal to 2.5, a content of persulfates in the polyacrylic acid polymer salt or in the liquid formulation of the polyacrylic acid polymer salt less than 0.005%, preferably less than 0.001%, w/w, based on the total dry weight of said polyacrylic acid polymer salt and a content of acrylic acid monomer in free acid form or salt form in the polyacrylic acid polymer salt or in the liquid formulation of the polyacrylic acid polymer salt less than 0.005% w/w, based on the total dry weight of said polyacrylic acid polymer salt; advantageously, this polyacrylic acid polymer salt has a Mark Houwink slope higher or equal to 0.7, or a weight average molecular weight Mw in the range of 400 to 600 kDa and a polydispersity index below or equal to 4, a content of persulfates in the polyacrylic acid polymer salt or in the liquid formulation of the polyacrylic acid polymer salt less than 0.005%, preferably less than 0.001%, w/w, based on the total dry weight of said polyacrylic acid polymer salt and a content of acrylic acid monomer in free acid form or salt form in the polyacrylic acid polymer salt or in the liquid formulation of the polyacrylic acid polymer salt less than 0.005% w/w, based on the total dry weight of said polyacrylic acid polymer salt; advantageously, this polyacrylic acid polymer salt has a Mark Houwink slope higher or equal to 0.7, or a weight average molecular weight Mw in the range of 400 to 600 kDa and a polydispersity index below or equal to 2, a content of persulfates in the polyacrylic acid polymer salt or in the liquid formulation of the polyacrylic acid polymer salt less than 0.005%, preferably less than 0.001%, w/w, based on the total dry weight of said polyacrylic acid polymer salt and a content of acrylic acid monomer in free acid form or salt form in the polyacrylic acid polymer salt or in the liquid formulation of the polyacrylic acid polymer salt less than 0.005% w/w, based on the total dry weight of said polyacrylic acid polymer salt; advantageously, this polyacrylic acid polymer salt has a Mark Houwink slope higher or equal to 0.7.

Advantageously, the polyacrylic acid polymer salt under the liquid formulation is diafiltered.

Advantageously, the polyacrylic acid polymer salt or the liquid formulation of the polyacrylic acid polymer salt is sterilized. When, the polyacrylic acid polymer salt or the liquid formulation of the polyacrylic acid polymer salt is diafiltered, the sterilization occurs after the diafiltration.

According to the invention, the weight average molecular weight Mw is obtained by size exclusion chromatography. Advantageously, three detectors will be used after the size exclusion chromatography column: a right angle light scattering detector, a refractive index detector and a four-capillary differential viscometer. The detailed procedures which are provided in the examples are preferably used according to the invention for the determination of the Mw, IP (polydispersity index), polymer concentration and Mark Houwink slope. The do/dc used for the determination of Mw is preferably determined using the refractive index detector with a panel of polyacrylic acid polymers of known concentration.

The content of persulfate and the content of acrylic acid monomer in free acid form or salt form can be determined by High Performance Anion Exchange Chromatography with conductimetric detection. Preferably, the protocol which is detailed in the examples, in particular in paragraph B of "1.2 Determination of persulfates and acrylate monomers" may be used.

Preparation and Storage of the Polyacrylic Acid Polymer

In polyacrylic acid polymer raw material, there is residual monomer content which corresponds to acrylic acid or acrylate salt content which did not polymerize. In polymerization of polyacrylic acid polymer, an initiator of polymerization, most of the time an oxidizing agent such as persulfates, is used as a catalyst to initiate the polymerization. In polyacrylic acid polymer raw material, there may remain a residual content of initiator of polymerization (most of the time, oxidizing agent such as persulfate) which has not been consumed by the polymerization process.

Polyacrylic acid polymers on the markets are often lacking specifications about residual monomer, and oxidizing agent(s) contents and about their precise Mw and their oligomer content.

According to a preferred embodiment of the invention, it is proposed to systematically purify the purchased polyacrylic acid polymer raw material which will be used for the preparation of an adjuvant composition, in order to avoid the risk of having residual contents of such compounds that can be detrimental, considering the stability of the adjuvant compositions and vaccine compositions containing the adjuvant and/or the toxicity of the vaccine composition. Additionally, according to the invention, it was identified that an important content of oxidizing agent(s), such as persulfates, is detrimental to the stability of the polymer under heat treatment and prohibits sterilization by autoclaving.

The invention concerns a process for the preparation of a pharmaceutically acceptable salt of polyacrylic acid polymer, in particular of the pharmaceutically acceptable salt of polyacrylic acid polymer as defined in the paragraph "Features of the polyacrylic acid polymer" comprising the following successive steps:

a) having a solution of a polyacrylic acid polymer,
b) purifying the solution of the polyacrylic acid polymer, in order to eliminate impurities and
c) sterilizing the purified solution of the polyacrylic acid polymer.

In steps a), b) and c), the solution can be a solution of the polyacrylic acid polymer directly in the form of the desired pharmaceutically acceptable salt, or at least partly, in the form of its free acid form. If in step a), the solution is a solution of the polyacrylic acid polymer in its free acid form, a salification can be carried out after the purification of step b) and the sterilization of step c) performed on the solution of the desired pharmaceutically acceptable salt. It is also possible to carry out the sterilization of step c) on the solution of the polyacrylic acid polymer in its free acid form and to perform a salification after sterilization.

At any stage, if a salification is required, it may be obtained by the introduction of a base, like NaOH or KOH in the solution, depending on the desired salt.

For instance, the purification and/or the sterilization are carried out on a solution of a pharmaceutically acceptable salt of the polyacrylic acid polymer. This solution is, for instance, a buffered aqueous solution, in particular with a phosphate buffer or with a TRIS, Hepes, histidine or citrate buffer. The aqueous solution of the pharmaceutically acceptable salt of the polyacrylic acid polymer may also comprise one or several additional salts, such as NaCl. In such cases, the process according to the invention, for the preparation of a pharmaceutically acceptable salt of polyacrylic acid polymer, in particular of the pharmaceutically acceptable salt of polyacrylic acid polymer as defined in the paragraph "Features of the polyacrylic acid polymer", comprises the following successive steps:
a) having a solution of the selected pharmaceutically acceptable salt of a polyacrylic acid polymer,
b) purifying the solution of the polyacrylic acid polymer salt, in order to eliminate impurities and
c) sterilizing the obtained purified solution of the polyacrylic acid polymer salt.

Advantageously, the polyacrylic acid polymer of the solution of step a) has a Mark Houwink slope higher or equal to 0.7. When in the solution, the polyacrylic acid polymer is in the form of a salt, this Mark Houwink slope concerns the polyacrylic acid polymer salt.

The purification will remove small molecules. The purification may be performed by dialysis, diafiltration, ultrafiltration or size exclusion chromatography. Diafiltration and ultrafiltration use cross-flow filtration (also called tangential flow filtration) on a porous membrane. A solution containing the polyacrylic acid polymer circulates on the membrane: a part of the solution including the small molecules is eliminated in the permeate which will pass through the membrane. Another part of the solution, called the retentate, including the purified polyacrylic polymer, will circulate on the surface of the membrane. The retentate can circulate in a circulation loop and be diafiltered or ultrafiltered several times. Solvent (typically aqueous buffer or saline aqueous solution) is added to the retentate which circulates, to replace the permeate volume, at the same rate as the permeate flow rate, such that the volume of the retentate remains constant. The size of the eliminated molecules is determined by the cut-off of the membrane. Advantageously, membranes with a cut-off from 1 to 80 kDa, preferably from 2 to 50 kDa, may be used. Such membranes are for instance available at Merck Millipore. The cut-off of a membrane is rated according to its Nominal Molecular Weight Limit (NMWL) or its Molecular Weight Cut Off (MWCO). For example, a UF membrane rated at 30 kD will exclude a test protein with a molecular weight of 30 kiloDaltons. Ninety percent of that test protein will remain in the retentate and 10% will pass through into the permeate, resulting in concentration of the protein if no buffer or saline solution is added to the retentate during the process.

Usually, the flow of retentate circulation is from 50 to 80 L/H/m$^2$. The Transmembrane Pressure (TMP) is, for instance, at 0.9+/−0.1 bar.

So, the purification in step b) may be carried out by dialysis, diafiltration, ultrafiltration or size exclusion chromatography. The purification may be performed on a solution containing from 2 to 50 mg/ml, preferably, from 10 to 30 mg/ml of the polyacrylic acid polymer. When, in the solution, the polymer is in the form of a salt, this concentration concerns the polymer salt.

Advantageously, the purification is carried out by diafiltration with a membrane having a cut-off from 1 to 80 kDa, preferably from 2 to 50 kDa.

Preferably, the purification is carried out in conditions allowing the recovery of a polyacrylic acid polymer in solution having:
less than 0.005%, preferably less than 0.001% w/w of persulfates, based on the total dry matter of the solution obtained after purification (in particular by diafiltration), or more generally, less than 0.005%, preferably than 0.001% w/w of oxidizing agents, based on the total dry matter of the solution obtained after purification (in particular by diafiltration), and/or
less than 0.005% w/w of acrylic acid monomer in free acid form or salt form, based on the total dry matter of the solution obtained after purification (in particular by diafiltration).

The weight average molecular weight Mw of the recovered polyacrylic acid polymer may be in the range of 350 to 650 kDa and its polydispersity index below or equal to 4.

The purification device will be chosen in order to eliminate the desired impurities. For instance, when ultrafiltration or diafiltration is used for purification, the cut-off of the membrane will be chosen, depending on the impurities to eliminate. With a cut-off of at least 20 kDa, essentially, the small molecules like persulfates and monomers are eliminated by cross-filtration. With a cut-off higher than 20 kDa, bigger molecules like oligomers are also eliminated and, as a result, the purification leads to a decrease of the IP and to an increase of the Mw.

Preferably, the diafiltration or ultrafiltration is carried out with a cut-off for the membrane used, or more generally the purification is carried out in conditions, allowing the recovery of a polyacrylic acid polymer in solution having: a weight average molecular weight Mw in the range of 380 to 620 kDa and a polydispersity index below or equal to 2.5; or a weight average molecular weight Mw in the range of 400 to 600 kDa and a polydispersity index below or equal to 2, and less than 0.005%, preferably less than 0.001% w/w of persulfates, based on the total dry matter of the solution obtained after purification (in particular by diafiltration), or more generally, less than 0.005%, preferably less than 0.001% w/w of oxidizing agents, based on the total dry matter of the solution obtained after purification (in particular by diafiltration), and/or less than 0.005% w/w of acrylic acid monomer in free acid form or salt form, based on the total dry matter of the solution obtained after purification (in particular by diafiltration).

Advantageously, the solution obtained after the purification steps contains from 2 to 50 mg/mL of the polyacrylic acid polymer salt, in particular at least 10 mg/ml of the polyacrylic acid polymer salt.

The main result of the purifying process is the elimination of small molecules, such as oxidizing agent (i.e. persulfate) and acrylate monomers.

By systematically carrying out such a purifying step, the characteristics of the polymer composition that is used as an adjuvant can be better defined and the composition is safer and more stable. The content of acrylic acid monomer which is suspected of being embryotoxic and teratogenic, is considerably reduced.

As explained above, depending on the device use (cut-off of the membrane in particular) diafiltration, dialysis, ultrafiltration or size exclusion chromatography also lead to the increase of the weight average molecular weight of the obtained polyacrylic acid polymer and to the decrease of its polydispersity index (IP). Indeed, depending on the used technique, and in particular of the cut-off of the used membrane, in diafiltration, dialysis and ultrafiltration, or of the permeation characteristics of the gel used in the size exclusion chromatography, oligomers are also eliminated and as a consequence, the Mw will be increased and the IP decreased. In these cases, the composition of the polymer salt is even more controlled.

The sterilization may be performed by sterilizing filtration(s) or preferably, by autoclaving. Sterilizing filtration is performed on a 0.2 μm pore membrane. The elimination of the oxidizing agent allows the use of sterilization by autoclaving which is recommended by Pharmacopeias. The autoclaving can be performed at a temperature from 100 to 150° C., and during a time from 5 minutes to one hour. With the purifying step, the obtained polymer is more stable in time and more resistant to heat treatment.

The invention also concerns a process for the storage of a solution of a pharmaceutically acceptable salt of polyacrylic acid polymer, in particular of the pharmaceutically acceptable salt of polyacrylic acid polymer as defined in the paragraph "Features of the polyacrylic acid polymer", comprising the preparation process as defined according to the invention, followed by a storage step of the obtained pharmaceutically acceptable salt of the polyacrylic acid polymer, in solution. The storage step may last from 1 day to 2 years. The temperature of storage will be, most of the time, in the range of 0 to 30° C., in particular at 2-8° C. or at room temperature, generally around 22° C. The storage can be performed directly after the step c) of sterilizing.

Such a storage of the adjuvant in a liquid form is very advantageous and avoids additional manipulations, by comparison to a storage in dry form which necessitates polymer resuspension/dilution for the preparation of the vaccine composition.

In particular, when the liquid solution of the polyacrylic acid polymer salt comprises less than 0.005%, preferably less than 0.001% w/w of oxidizing agents, based on the total dry weight of said polyacrylic acid polymer salt and/or less than 0.005%, preferably less than 0.001% w/w of persulfates, based on the total dry weight of said polyacrylic acid polymer salt, the solution is particularly stable.

The storage step is carried out by placing the solution of the polyacrylic acid polymer salt in a container and storing it. During the storage, the stored solution, for instance, contains from 2 to 50 mg/mL of the polyacrylic acid polymer salt. A dilution or a concentration step can be carried out for obtaining the desired concentration, for instance after step b) of the preparation process. During the storage, the polyacrylic acid polymer salt may be, for instance, in an aqueous solution or in a buffered aqueous solution. The pH of the stored solution is usually between 5.5 and 8, and more preferably between 6.5 and 7.5 (e.g. about 7). Stable pH may be maintained by the use of a buffer e.g. a Tris buffer, a citrate buffer, phosphate buffer, a Hepes buffer, or a histidine buffer.

The aqueous solution may also comprise one or several additional salts, such as NaCl.

The storage can be performed by keeping the solution of the polyacrylic acid polymer salt away from light. For that, a dark or opaque container can be used.

Use of Polyacrylic Acid Polymer, as an Adjuvant

The invention also concerns the polyacrylic acid polymer salt, as defined in the invention, whatever the described embodiment in relation with the above paragraph "Features of the polyacrylic acid polymer" for its use as an adjuvant in a vaccine composition or for its use as an adjuvant to a vaccine agent in raising an immune response in an individual, in particular in a human being.

An adjuvant composition for vaccine, comprising an aqueous solution of a pharmaceutically acceptable salt of polyacrylic acid polymer, as defined in the invention, whatever the described embodiment in relation with the above paragraph "Features of the polyacrylic acid polymer" is also an object of the invention.

"Adjuvant", as used herein, refers to a compound that modulates the immunogenicity of a vaccine composition. A vaccine composition classically includes a vaccine agent which can be an antigen or a vector (live recombinant viral vector or nucleic acid) encoding an antigen. More precisely, an adjuvant modulates the immunogenicity of the antigen present or encoded by the nucleic acid present in the composition. "Modulate the immunogenicity" includes enhancing the magnitude and/or duration of an immune response induced by the antigen, and includes in particular the enhancement of the antibody response (especially virus neutralizing antibodies or bactericidal antibodies) and/or the enhancement of the cellular immune responses (enhancement of CD4+ and/or CD8+ T cell responses).

The polymer selected according to the invention has different advantages, as shown by the examples. For instance, in comparison with analogous linear or ramified polymers of lower Mw, they lead to increased immune responses.

CD4+ lymphocytes, also called "helper" T cells, are immune response mediators. Classically, two types of effector CD4+T helper cell responses, designated Th1 and Th2, are characterized by cytokine profiling and antibody subtyping. The use of the polyacrylic acid polymer, as defined in the invention, has the advantage to promote strong Th-1 responses (results on IFN-γ, TNF-α and IgG2a antibodies in mice were obtained) in addition to the Th-2 responses (results on 11-4, IL-5 and IgG1 antibodies in mice were obtained) that are commonly induced by human adjuvants of the prior art (aluminum salts, oil-in-water emulsions). The induction of strong Th-1 immunity is important to fight viral and intracellular bacterial infections, as well as cancer, since Th-1 immune responses support the activation of macrophages and of other killer cells (e.g. CD8+T lymphocytes or Cytotoxic T Lymphocytes) to kill intracellular pathogens, infected cells and tumor cells.

The polyacrylic acid polymer salt of the invention and the vaccine agent can be formulated in a same composition, in particular in an aqueous composition, or in two different compositions and mixed just before administration.

It is also possible to have a vaccine composition in the form of a kit of parts. The vaccine composition can include two vials: one contains the vaccine agent and the other contains the polyacrylic acid polymer salt. In particular, the polyacrylic acid polymer salt in a liquid formulation is contained in a first vial and the vaccine agent in a freeze-dried or lyophilized form, in particular the selected antigen in a freeze-dried or lyophilized form, is contained in a second vial. The formulation of the polyacrylic acid polymer salt will be used for rehydrating the vaccine agent, in particular the selected antigen.

The invention also concerns the polyacrylic acid polymer salt, as defined in the invention, whatever the described embodiment in relation with the above paragraph "Features of the polyacrylic acid polymer" for its use as an adjuvant in a vaccine composition which enhances the obtained Th1 immune response and/or which balances the obtained Th1 and Th2 immune responses. In particular, the polyacrylic acid polymer salt, as defined in the invention, is used as an adjuvant to a vaccine agent for raising the immune response in an individual, in particular in a human being, and enhancing the obtained Th1 immune response and/or balancing the obtained Th1 and Th2 immune responses.

Vaccine Composition and Vaccine Agent

The vaccine composition according the invention may comprise any vaccine agent that can be used in a vaccine, such as an antigen or a vector (live viral vector or nucleic acid, including DNA and RNA) encoding an antigen.

For the purpose of the present invention, the term "antigen" is intended to mean any molecule containing one or more epitopes (either linear, conformational or both), that elicits an immunological response. The antigen(s) which can be used in a vaccine composition according to the invention can be a living, attenuated, killed, inactivated or non-infectious whole microorganism, an extract or split of a microorganism, a subunit form of a natural antigen, a recombinant form or a hybrid form. When it is a subunit form, the nature of the antigen is of little importance. The antigen may be a peptide, a protein, a glycoprotein, a polysaccharide, a glycolipid, a lipoprotein, a lipopeptide, a VLP (virus-like particle) . . . etc.

The vaccine agent present in the composition is an antigen or a vector (recombinant virus or nucleic acid) encoding an antigen used or suitable to be used for the treatment or prevention of various diseases that may affect humans or animals other than humans, notably including: diphtheria, tetanus, polio, rabies, whooping cough, hepatitis A, hepatitis B, hepatitis C, yellow fever, typhoid fever, chickenpox, measles, mumps, rubella, Japanese encephalitis, influenza, meningitis, cholera, infections caused by Rotavirus, Norovirus, Rhinovirus, Respiratory Syncytial Virus, Herpes Simplex Virus, Papilloma Virus, cytomegalovirus virus, West Nile Virus, Dengue Virus, Chykungunya Virus, HIV (AIDS), bacterial diseases caused by streptococci, *Chlamydia trachomatis* and *pneumoniae, Neisseria gonorrhoeae* and *meningitidis, Moraxella catarrhalis, Staphylococcus aureus,* or *Haemophilus influenza* type B, the listeriosis, shigellosis, *salmonellosis,* tuberculosis, Lyme disease, cancer, parasitic diseases such as malaria, Leishmaniasis, Chagas disease, schistosomiasis . . . etc.

The antigens can be of bacterial, viral or parasitic nature. Among the antigens that are suitable for the subject of the invention, mention is made of the bacterial antigens originated from *Clostridium tetani, Clostridium diphtherias, Bordetella pertussis, Haemophilus influenzae* type B, *Streptococcus pneumoniae, Neisseria meningitidis, Shigella* sp, *Salmonella typhi, Staphylococcus aureus* or *Staphylococcus epidermidis, Mycobacterium tuberculosis, Chlamydia trachomatis* and *pneumoniae* or *Streptococcus* sp, the viral antigens originated from the hepatitis A, B or C virus, the influenza virus, the rhinovirus, the respiratory syncytial virus, the West Nile virus, the rabies virus, the poliovirus, the HIV virus, the dengue virus, the Japanese encephalitis virus, the yellow fever virus, the cytomegalovirus or the herpes virus, the parasitic antigens originated in particular from *Plasmodium* sp., *leishmania* sp. or *schistosoma* sp. and the tumor antigens. These antigens can be obtained using genetic recombination methods or using extraction methods well-known to those skilled in the art.

In particular, the vaccine agent present in the composition is an antigen or a vector (recombinant virus or nucleic acid) encoding an antigen originated from *Staphylococcus aureus,* or from the cytomegalovirus.

The vaccine composition of the invention may be a composition intended for immunization against a single pathogen or cancer, that is to say it comprises one or more vaccine agents, in particular one or more antigens, of a single pathogen or cancer, or may be a composition intended for immunization against several pathogens or cancers.

The vaccine composition according to the invention may also include one or several specific vaccine agents, in particular one or several antigens of a single disease, but which belong to different categories of this disease (multiple serotypes or strains, or clades, depending on the nature of the agent).

The polyacrylic acid polymer salt of the invention and the vaccine agent can be formulated in a composition with any pharmaceutically acceptable vehicle. In the context of the invention, the expression "pharmaceutically acceptable vehicle" refers to a vehicle that is physiologically acceptable for administration to a mammal, and in particular to a human being, while retaining the physiological activity of the composition according to the invention, i.e. its ability to induce an immune response. One exemplary pharmaceutically acceptable vehicle is a physiological saline buffer. Other physiologically acceptable vehicles are known to those skilled in the art and are described, for instance, in Remington's Pharmaceutical Sciences ($18^{th}$ edition), ed. A. Gennaro, 1990, Mack Publishing Company, Easton, Pa.

The pH of the composition is usually between 5.5 and 8, and more preferably between 6.5 and 7.5 (e.g. about 7). Stable pH may be maintained by the use of a buffer e.g. a Tris buffer, a citrate buffer, phosphate buffer, a Hepes buffer, or a histidine buffer. Thus, the composition generally includes a buffer. The composition may be sterile and/or pyrogen-free. Compositions may be isotonic with respect to humans.

The composition may also comprise one or several additional salts, such as NaCl.

A composition according to the invention comprises an immunologically effective amount of the vaccine agent. An "immunologically effective amount" is an amount which, when administered to a subject, is effective for eliciting an immune response against the antigen used or generated upon vector and/or nucleic acid expression. This amount can vary depending on the health and physical condition of the subject to be treated, their age, the capacity of the subject's immune system to produce antibodies, the degree of protection desired, the formulation of the vaccine, the treating doctor's assessment of the medical situation.

The vaccine composition according to the invention may also comprise allergen(s), in particular allergen(s) for desensitization in the treatment of allergies.

The vaccine composition according to the invention may be administered by any route commonly used for administering a vaccine. A regimen leading to the induction of the expected immune response will be used. Usually, the immunization schedule includes several administrations. The amount of the composition administered is enough to produce the desired immune response.

Preferably, the vaccine composition is in a liquid form considering the good stability properties of the polyacrylic acid polymer allowing the use of liquid forms which are less expensive to produce.

The parenteral injections (intramuscular, subcutaneous, intradermal and intravenous) are also preferred. The polyacrylic acid polymer does not cause local apparent side effects after an intradermal injection. This can be an advantage over most other adjuvants (including aluminum salts) that are sometimes reactogenic through intradermal route.

Preferred vaccine compositions according to the invention are described hereafter:

A vaccine composition according to the invention comprises at least one vaccine agent and a pharmaceutically acceptable salt of polyacrylic acid polymer, said polyacrylic acid polymer salt having a weight average molecular weight Mw in the range of 350 to 650 kDa.

Advantageously, the vaccine composition according to the invention comprises per dose from 0.1 to 8 mg of the pharmaceutically acceptable salt of the polyacrylic acid polymer, preferably from 0.1 to 4 mg, and more preferably from 0.1 to 2 mg.

Preferably, at least one vaccine agent is an antigen or a vector (viral vector or nucleic acid) encoding an antigen, the said antigen being a bacterial antigen originated from *Clostridium tetani, Clostridium diphtheriae, Bordetella pertussis, Haemophilus influenzae* type B, *Streptococcus pneumoniae, Neisseria meningitidis, Shigella* sp, *Salmonella typhi, Staphylococcus aureus* or *Staphylococcus epidermidis, Mycobacterium tuberculosis, Chlamydia trachomatis* or *pneumoniae* or *Streptococcus* sp; a viral antigen originated from the hepatitis A, B or C virus, the influenza virus, the rhinovirus, the respiratory syncytial virus, the West Nile virus, the rabies virus, the poliovirus, the HIV virus, the dengue virus, the Japanese encephalitis virus, the yellow fever virus, the cytomegalovirus or the herpes virus; a parasitic antigen originated in particular from *Plasmodium* sp., *leishmania* sp. or *schistosoma* sp. or a tumor antigen. In particular, the vaccine agent present in the composition is an antigen or a vector (recombinant virus or nucleic acid) encoding an antigen originated from *Staphylococcus aureus*, or from the cytomegalovirus.

In a preferred embodiment, the vaccine compositions according to the invention are in a liquid form having a pH in the range of 5.5 to 8.0. For instance, they include a phosphate buffer or a TRIS, Hepes, histidine or citrate buffer.

The polyacrylic acid polymer salt present in the vaccine composition has one of the following characteristics, any combination of such characteristics or even all the following characteristics if they do not exclude one another:

the polyacrylic acid polymer salt or the liquid formulation of the polyacrylic acid polymer salt comprises less than 0.005%, preferably less than 0.001% w/w of oxidizing agents, based on the total dry weight of said polyacrylic acid polymer salt and/or less than 0.005%, preferably less than 0.001% w/w of persulfates, based on the total dry weight of said polyacrylic acid polymer salt;

the polyacrylic acid polymer salt has a polydispersity index below or equal to 4, preferably below or equal to 2.5;

the polyacrylic acid polymer salt has a weight average molecular weight Mw in the range of 380 to 620 kDa and a polydispersity index below or equal to 4 or has a weight average molecular weight Mw in the range of 400 to 600 kDa and a polydispersity index below or equal to 4;

the polyacrylic acid polymer salt has a weight average molecular weight Mw in the range of 380 to 620 kDa and a polydispersity index below or equal to 2.5 or has a weight average molecular weight Mw in the range of 400 to 600 kDa and a polydispersity index below or equal to 2;

the polyacrylic acid polymer salt has a Mark Houwink slope higher or equal to 0.7;

the polyacrylic acid polymer salt or the liquid formulation of the polyacrylic acid polymer salt comprises less than 0.005% w/w of acrylic acid monomer in free acid form or salt form, based on the total dry weight of said polyacrylic acid polymer salt, the pharmaceutically acceptable salt of the linear or branched polyacrylic acid polymer is diafiltered and/or is sterilized.

In particular, the polyacrylic acid polymer salt present in the vaccine composition is characterized by:

a weight average molecular weight Mw in the range of 380 to 620 kDa and a polydispersity index below or equal to 4, a content of persulfates in the polyacrylic acid polymer salt or in the liquid formulation of the polyacrylic acid polymer salt less than of 0.005%, preferably less than 0.001% w/w, based on the total dry weight of said polyacrylic acid polymer salt and a content of acrylic acid monomer in free acid form or salt form in the polyacrylic acid polymer salt or in the liquid formulation of the polyacrylic acid polymer salt less than 0.005% w/w, based on the total dry weight of said polyacrylic acid polymer salt; advantageously, this polyacrylic acid polymer salt has a Mark Houwink slope higher or equal to 0.7, or a weight average molecular weight Mw in the range of 380 to 620 kDa and a polydispersity index below or equal to 2.5, a content of persulfates in the polyacrylic acid polymer salt or in the liquid formulation of the polyacrylic acid polymer salt less than 0.005%, preferably less than 0.001% w/w, based on the total dry weight of said polyacrylic acid polymer salt and a content of acrylic acid monomer in free acid form or salt form in the polyacrylic acid polymer salt or in the liquid formulation of the polyacrylic acid polymer salt less than 0.005% w/w, based on the total dry weight of said polyacrylic acid polymer salt; advantageously, this polyacrylic acid polymer salt has a Mark Houwink slope higher or equal to 0.7, or a weight average molecular weight Mw in the range of 400 to 600 kDa and a polydispersity index below or equal to 4, a content of persulfates in the polyacrylic acid polymer salt or in the liquid formulation of the polyacrylic acid polymer salt less than 0.005%, preferably less than 0.001% w/w, based on the total dry weight of said polyacrylic acid polymer salt and a content of acrylic acid monomer in free acid form or salt form in the polyacrylic acid polymer salt or in the liquid formulation of the polyacrylic acid polymer salt less than 0.005% w/w, based on the total dry weight of said polyacrylic acid polymer salt; advantageously, this polyacrylic acid polymer salt has a Mark Houwink slope higher or equal to 0.7, or a weight average molecular weight Mw in the range of 400 to 600 kDa and a polydispersity index below or equal to 2, a content of persulfates in the polyacrylic acid polymer salt or in the liquid formulation of the polyacrylic acid polymer salt less than 0.005%, preferably less than 0.001% w/w, based on the total dry weight of said polyacrylic acid polymer salt and a content of acrylic acid monomer in free acid form or salt form in the polyacrylic acid polymer salt or in the liquid formulation of the polyacrylic acid polymer salt less than 0.005% w/w, based on the total dry weight of said polyacrylic acid polymer salt; advantageously, this polyacrylic acid polymer salt has a Mark Houwink slope higher or equal to 0.7.

The invention also relates to the vaccine compositions of the invention for their use in raising an immune response in an individual, in particular in a human being. The subject matter of the invention also encompasses a method of raising an immune response in an individual, in particular, in a human being, comprising the step of administering to the individual in need thereof an immunologically effective amount of the composition according to the invention. The individual can be a human being or an animal selected from a canine, a feline, a bovine, a porcine, an equine or an ovine species as well as the mustelids and the avian species.

The invention also relates to the vaccine compositions of the invention for their use in raising an immune response in an individual, in particular in a human being, with enhancement of the obtained Th1 immune response The subject matter of the invention also encompasses a method of raising an immune response in an individual, in particular, in a human being, with enhancement of the obtained Th1 immune response, said method comprising the step of administering to the individual in need thereof an immunologically effective amount of the composition according to the invention.

Preparation of the Vaccine Composition

Advantageously, the polyacrylic acid polymer or the polyacrylic acid polymer salt has been subjected to a purification, such as diafiltration, prior to its addition into the vaccine composition. More precisely, the polyacrylic acid polymer or the polyacrylic acid polymer salt has been subjected to a purification, such as diafiltration, followed by a sterilization, prior to its introduction into the vaccine composition. The sterilization may be performed by sterilizing filtration(s) or, preferably, by autoclaving.

According to the invention, the vaccine composition can be prepared by simply mixing the polyacrylic acid polymer salt, in particular in a liquid form in an aqueous solution or in a buffered aqueous solution, and a suspension of the vaccine agent(s) and other component(s) that can be present in the composition. This can be done by adding one or more selected vaccine agents on the polyacrylic acid polymer salt, in particular on the polyacrylic acid polymer salt in a liquid formulation in an aqueous solution or in a buffered aqueous solution, or by adding the polyacrylic acid polymer, in particular the polyacrylic acid polymer in a liquid formulation in an aqueous solution or in a buffered aqueous solution, on a suspension already comprising the selected vaccine agent(s). On the other hand, in the case where it is desired to formulate vaccine compositions comprising multiple vaccine agents, it may be preferred to perform firstly the mixing of the polyacrylic acid polymer salt with one or more vaccine agent(s), and to incorporate the other(s) after.

Alternatively, if the vaccine agent is formulated as a freeze-dried or lyophilized product, the vaccine composition can be obtained by rehydration of the lyophilized agent(s) directly with the formulation (aqueous solution or buffered aqueous solution) containing the polyacrylic acid polymer salt.

The invention also concerns the use of the polyacrylic acid polymer salt, as defined in the invention, whatever the described embodiment in relation with the above paragraph "Features of the polyacrylic acid polymer", in the preparation of a vaccine composition comprising at least one vaccine agent.

A process of a vaccine composition implementing the mixing of the polyacrylic acid polymer salt, as defined in the invention, whatever the described embodiment in relation with the above paragraph "Features of the polyacrylic acid polymer", with at least one vaccine agent, is also an object of the invention.

For convenience, certain terms employed in the Specification, Examples, and appended Claims are collected here.

As used herein, the term "animal" includes all vertebrate animals including humans. It also includes an individual animal in all stages of development, including embryonic and fetal stages. In particular, the term "vertebrate animal" includes, but not limited to, humans, canines (e.g., dogs), felines (e.g., cats); equines (e.g., horses), bovines (e.g., cow, cattle), porcine (e.g., pigs), as well as in avians. As used herein, the term "cow" or "cattle" is used generally to refer to an animal of bovine origin of any age. Interchangeable terms include "bovine", "calf", "steer", "bull", "heifer", "cow" and the like. Interchangeable terms include "piglet", "sow" and the like. The term "avian" as used herein refers to any species or subspecies of the taxonomic class ava, such as, but not limited to, chickens (breeders, broilers and layers), turkeys, ducks, a goose, a quail, pheasants, parrots, finches, hawks, crows and ratites including ostrich, emu and cassowary. The term "pig" or "piglet" means an animal of porcine origin, while "sow" refers to a female of reproductive age and capability.

As used herein, the term "virulent" means an isolate that retains its ability to be infectious in an animal host.

As used herein, the term "inactivated vaccine" means a vaccine composition containing an infectious organism or pathogen that is no longer capable of replication or growth. The pathogen may be bacterial, viral, protozoal or fungal in origin. Inactivation may be accomplished by a variety of methods including freeze-thawing, chemical treatment (for example, treatment with formalin), sonication, radiation, heat or any other convention means sufficient to prevent replication or growth of the organism while maintaining its immunogenicity.

As used herein, the term "immunogenicity" means capable of producing an immune response in a host animal against an antigen or antigens. This immune response forms the basis of the protective immunity elicited by a vaccine against a specific infectious organism.

As used herein, the term "immune response" refers to a response elicited in an animal. An immune response may refer to cellular immunity (CMI); humoral immunity or may involve both. The present invention also contemplates a response limited to a part of the immune system. For example, a vaccine composition of the present invention may specifically induce an increased gamma interferon response.

As used herein, the term "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a protein, a polypeptide, a peptide, an epitope, a hapten, toxin, antitoxin; or any combination thereof.

As used herein, the term "multivalent" means a vaccine containing more than one antigen whether from the same species (i.e., different isolates of FMD virus serotypes), from a different species (i.e., isolates from both *Pasteurella haemolytica* and *Pasteurella multocida*), or a vaccine containing a combination of antigens from different genera (for example, a vaccine comprising antigens from *Pasteurella multocida, Salmonella, Escherichia coli, Haemophilus somnus* and *Clostridium*).

As used herein, the terms "pharmaceutically acceptable carrier" and "pharmaceutically acceptable vehicle" are interchangeable and refer to a fluid vehicle for containing vaccine antigens that can be injected into a host without adverse effects. Suitable pharmaceutically acceptable carriers known in the art include, but are not limited to, sterile water, saline, glucose, dextrose, or buffered solutions. Carriers may include auxiliary agents including, but not limited to, diluents, stabilizers (i.e., sugars and amino acids), preservatives, wetting agents, emulsifying agents, pH buffering agents, viscosity enhancing additives, colors and the like.

As used herein, the term "vaccine composition" includes at least one antigen or immunogen in a pharmaceutically acceptable vehicle useful for inducing an immune response in a host. Vaccine compositions can be administered in dosages and by techniques well known to those skilled in the medical or veterinary arts, taking into consideration such factors as the age, sex, weight, species and condition of the recipient animal, and the route of administration. The route of administration can be percutaneous, via mucosal administration (e.g., oral, nasal, anal, vaginal) or via a parenteral route (intradermal, intramuscular, subcutaneous, intravenous, or intraperitoneal). Vaccine compositions can be administered alone, or can be co-administered or sequentially administered with other treatments or therapies. Forms of administration may include suspensions, syrups or elixirs, and preparations for parenteral, subcutaneous, intradermal, intramuscular or intravenous administration (e.g., injectable administration) such as sterile suspensions or emulsions. Vaccine compositions may be administered as a spray or mixed in food and/or water or delivered in admixture with a suitable carrier, diluent, or excipient such as sterile water, physiological saline, glucose, or the like. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. Standard pharmaceutical texts, such as "Remington's Pharmaceutical Sciences," 1990 may be consulted to prepare suitable preparations, without undue experimentation.

The immunogen or antigen suitable for use in the present invention may be selected from the group consisting of inactivated pathogens, attenuated pathogens, immunogenic sub-units (e.g. proteins, polypeptides, peptides, epitopes, haptens), or recombinant expression vectors, including plasmids having immunogenic inserts. In one embodiment of the present invention, the immunogen is an inactivated or killed microorganism. In another embodiment of the invention, the vaccine composition comprises an immunogen selected from the group of avian pathogens including, but not limited to, *Salmonella typhimurium, Salmonella enteritidis*, Infectious Bronchitis virus (IBV), Newcastle Disease virus (NDV), egg drop syndrome virus (EDS), or Infectious Bursal Disease virus (IBDV), avian influenza virus, and combinations thereof.

Alternately, the vaccine composition comprises an immunogen selected from a feline pathogen such as feline herpesvirus (FHV), feline calicivirus (FCV), feline leukemia virus (FeLV), feline immunodeficiency virus (FIV), rabies virus, and combinations thereof.

In yet another embodiment, a vaccine composition of the present invention comprises an immunogen selected from a canine pathogen including, but not limited to, rabies virus, canine herpesvirus (CHV), canine parvovirus (CPV), canine coronavirus, *Leptospira canicola, Leptospira icterohaemorragiae, Leptospira grippotyphosa, Borrelia burgdorferi, Bordetella bronchiseptica* and the like, and combinations thereof.

In yet another embodiment of the invention the composition comprises an immunogen selected from an equine pathogen, such as equine herpesvirus (type 1 or type 4), equine influenza virus, tetanus, west nile virus, and the like or combinations thereof.

In yet another embodiment of the invention, the composition comprises an immunogen selected from an bovine pathogen, such as foot and mouth disease virus (FMDV), rabies virus, bovine rotavirus, bovine parainfluenza virus type 3 (bPIV-3), bovine coronavirus, bovine viral diarrhea virus (BVDV), bovine respiratory syncytial virus (BRSV), Infectious Bovine Rhinotracheitis virus (IBR), *E. coli, P. multocida, P. haemolytica* and combinations thereof.

In still another embodiment of the present invention, the composition comprises a vaccine agent, including immunogens and nucleic acids encoding immunogens, selected from an porcine pathogen such as, but not limited to, swine influenza virus (SIV), porcine circovirus type 2 (PCV-2), porcine reproductive respiratory syndrome virus (PRRS), pseudorabies virus (PRV), porcine parvovirus (PPV), FMDV, *M. hyopneumoniae, Erysipelothrix rhusiopathiae, Pasteurella multocida, Bordetella bronchiseptica, E. coli* and the like, and combinations thereof.

Vaccine agents comprising viruses, bacteria, fungi and the like may be produced by in vitro culture methods using appropriate culture medium or host cells lines and conventional methods well known to those of ordinary skill in the art. For example, PRRS may be cultured in an appropriate cell line, such as MA-104 cell line (see U.S. Pat. Nos. 5,587,164; 5,866,401; 5,840,563; 6,251,404). In a similar manner, PCV-2 may be cultured using PK-15 cells line (see U.S. Pat. No. 6,391,314); SIV may be cultured on eggs (U.S. Pat. No. 6,048,537); and *M. hyopneumoniae* may be cultured in an appropriate culture medium (U.S. Pat. Nos. 5,968,525; 5,338,543).

In order to obtain an inactivated immunologic, or vaccine composition, the pathogen is preferably inactivated after harvesting and, optionally, subjected to clarification by means of a chemical treatment using, for example, formalin or formaldehyde, beta-propiolactone, ethyleneimine, binary ethyleneimine (BEI), and/or a physical treatment (e.g. a heat treatment or sonication). Methods for inactivation are well known to those of skill in the art. For example, the FMD virus may be inactivated by ethyleneimine (Cunliffe, H R, Applied Microbiology, 1973, p. 747-750) or by high pressure (Ishimaru et al., Vaccine 22 (2004) 2334-2339), the PRRS virus may be inactivated by beta-propiolactone treatment (Plana-Duran et al., Vet. Microbiol., 1997, 55: 361-370) or by BEI treatment (U.S. Pat. No. 5,587,164); inactivation of PCV-2 virus may be accomplished using ethyleneimine treatment or by beta-propiolactone treatment (U.S. Pat. No. 6,391,314); swine influenza virus may be inactivated using a detergent like Triton, or with formaldehyde treatment (U.S. Pat. No. 6,048,537); *M. hyopneumoniae* bacterium may be inactivated by formaldehyde treatment (Ross R. F. supra), by ethyleneimine or BEI treatment.

The inactivated pathogen can be concentrated by conventional concentration techniques, in particular by ultrafiltration, and/or purified by conventional purification means, in particular using chromatography techniques including, but not limited to, gel-filtration, ultracentrifugation on a sucrose gradient, or selective precipitations, in particular in the presence PEG.

Immunogens useful in vaccine compositions according to the present invention also include expression vectors. Such vectors include, but are not limited to, in vivo recombinant expression vectors such as a polynucleotide vector or a plasmid (EP-A2-1001025; Chaudhuri P, Res. Vet. Sci. 2001, 70: 255-6), virus vectors such as, but not limited to, adenovirus vectors, poxvirus vectors such as fowlpox (U.S. Pat. Nos. 5,174,993; 5,505,941; and 5,766,599) or canarypox vectors (U.S. Pat. No. 5,756,103) or bacterial vectors (*E. coli* or *Salmonella* sp.).

The present invention also encompasses the formulation of multivalent immunological compositions or combination vaccine compositions. For example, antigens useful in a combination bovine bacterin made according to the present invention include, but are not limited to, *Mycoplasma bovis, Pasteurella* sp., particularly *P. multocida* and *P. haemolytica, Haemophilus* sp., particularly *H. somnus, Clostridium* sp., *Salmonella, Corynebacterium, Streptococcus, Staphylococcus, Moraxella, E. coli* and the like.

The present invention further provides for methods for inducing an immune response in a host, e.g., an animal, comprising administering to the host an immunological composition or a vaccine composition according to the invention. The immune responses elicited in this manner are notably antibody and/or cellular immune responses, and in particular, a γ-interferon response.

In particular, the present invention provides for methods to immunize against, or to prevent or to reduce the symptoms caused by, infection of an animal with a pathogenic organism (for example, infection by a virus, bacteria, fungus, or protozoan parasite). The method of the present invention is useful in vertebrate animals including, but not limited to, humans, canines (e.g., dogs), felines (e.g., cats); equines (e.g., horses), bovines (e.g., cattle) and porcine animals (e.g., pigs), as well as in avians including, but not limited to, chickens, turkeys, ducks, geese, a quail, a pheasant, parrots, finches, hawks, crows and ratites (ostrich, emu, cassowary, etc.).

In a particular aspect of the invention, these methods consist of the vaccination of pregnant females before parturition by administering a vaccine composition made according to the invention. These methods further include the induction of protective antibodies elicited by the vaccination protocol and the transfer of these protective antibodies from vaccinated pregnant females to their offspring, to protect the offspring from infection and disease.

The dosage of the vaccine composition made according to the present invention will depend on the species, breed, age, size, vaccination history, and health status of the animal to be vaccinated. Other factors like antigen concentration, additional vaccine components, and route of administration (i.e., subcutaneous, intradermal, oral, intramuscular or intravenous administration) will also impact the effective dosage. The dosage of vaccine to administer is easily determinable based on the antigen concentration of the vaccine, the route of administration, and the age and condition of the animal to be vaccinated. Each batch of antigen may be individually calibrated. Alternatively, methodical immunogenicity trials of different dosages, as well as $LD_{50}$ studies and other screening procedures can be used to determine effective dosage for a vaccine composition in accordance with the present invention without undue experimentation. From the examples presented below, it will be readily apparent what approximate dosage and what approximate volume would be appropriate for using the vaccine composition described herein. The critical factor is that the dosage provides at least a partial protective effect against natural infection, as evidenced by a reduction in the mortality and morbidity associated with natural infection. The appropriate volume is likewise easily ascertained by one of ordinary skill in the art. For example, in avian species the volume of a dose may be from about 0.1 ml to about 0.5 ml and, advantageously, from about 0.3 ml to about 0.5 ml. For feline, canine and equine species, the volume of a dose may be from about 0.2 ml to about 3.0 ml, advantageously from about 0.3 ml to about 2.0 ml, and more advantageously, from about 0.5 ml to about 1.0 ml. For bovine and porcine species, the volume of dose may be from about 0.2 ml to about 5.0 ml, advantageously from about 0.3 ml to about 3.0 ml, and more advantageously from 0.5 ml to about 2.0 ml.

Repeated vaccinations may be preferable at periodic time intervals to enhance the immune response initially or when a long period of time has elapsed since the last dose. In one embodiment of the present invention, the vaccine composition is administered as a parenteral injection (i.e., subcutaneously, intradermally, or intramuscularly). The composition may be administered as one dose or, in alternate embodiments, administered in repeated doses of from about two to about five doses given at intervals of about two to about six weeks, preferably from about two to about five weeks. However, one of skill in the art will recognize that the number of doses and the time interval between vaccinations depends on a number of factors including, but not limited to, the age of the animal vaccinated; the condition of the animal; the route of immunization; amount of antigen available per dose; and the like. For initial vaccination, the period will generally be longer than a week and preferably will be between about two to about five weeks. For previously vaccinated animals, a booster vaccination, before or during pregnancy, at about an annual interval may be performed.

The invention further relates to methods to treat a host, e.g., an animal, comprising administering to the host a pharmaceutical composition made according to the invention and comprising at least one immunogen selected from the group consisting of proteins or peptides, inactivated or attenuated virus, antibodies, allergens, CpG ODN, growth factors, cytokines, or antibiotics, and in particular CpG ODN or cytokines. These pharmaceutical compositions can be used to improve growth performances in an animal such as a chicken, a pig, a cow or cattle.

In an embodiment, the disclosure provides an immunological or vaccine composition comprising an adjuvant formulation, a therapeutically effective amount of an antigen component, and a pharmaceutically or veterinarily acceptable carrier, wherein the adjuvant formulation comprises a non-crosslinked polyacrylic acid (PAA) polymer having a weight average molecular weight (AMw) of about 350 kDa to about 650 kDa. In some embodiments, the antigen component may comprise an attenuated recombinant viral vector, a naturally or genetically-engineered live attenuated virus or microorganism, an inactivated virus or microorganism, a coccidian microorganism, a precocious coccidian microorganism, a proteinaceous subunit, a single-celled parasite, a multi-cellular parasite or any combination of the preceding.

In a particular embodiment, the antigen component may comprise: a canine coronavirus (CCV) antigen, a canine distemper virus (CDV) antigen, a canine parvovirus antigen (CPV), a canine parainfluenza (CPI) antigen, a feline calicivirus (FCV) antigen, a feline immunodeficiency virus (FIV) antigen, a feline herpes virus (FHV) antigen, a feline leukemia virus (FeLV) antigen, a cancer antigen (e.g. Her2-neu, tyrosinase, 11-2 and the like), an *Eimeria* sp. or antigen thereof, *Escherichia coli* (*E. coli*) or antigen thereof, *Mycoplasma* hyopneumoniae (*M. hyo*), a bovine diarrhea virus (BDV) antigen, a recombinant canarypox vector containing and capable of in vivo expression of at least one protective immunogen, an inactivated full-length rabies glycoprotein, an *Erysipelothrix* sp., *Erysipelothrix rhusiopathiae*, a surface protective antigen (SpaA) from *E. rhusiopathiae*, a SpaA fusion protein comprising at least a portion of at least one additional immunogen, a SpaA-FlaB fusion protein, a SpaA-FlaB-His fusion protein, a *Clostridium* (*C.*) *perfringens* B/C toxin, a *C. perfringens* D toxin, *C. septicum* toxin, *C. novyi* toxin, a *C. tetani* toxin or any combination of the preceding.

In another embodiment, the antigen component comprises or consists of an inactivated full-length rabies glycoprotein. The antigen component may also comprise or consist of a *C. perfringens* B/C toxin, a *C. perfringens* D toxin, *C. septicum* toxin, *C. novyi* toxin, a *C. tetani* toxin or combinations thereof. In a particular embodiment, the immunological or vaccine composition may comprise an antigen component comprising a *C. perfringens* B/C toxin, a *C. perfringens* D toxin, *C. septicum* toxin, *C. novyi* toxin and a *C. tetani* toxin. The PAA adjuvant disclosed herein provides "dose sparing."

In yet another embodiment, the antigen component comprises a SpaA antigen or a fusion protein comprising the SpaA antigen.

In another embodiment, the antigen component comprises an attenuated avipox virus or a DNA plasmid containing and capable of in vivo expression of an influenza gene. The antigen component may also comprise an attenuated avipox virus or a DNA plasmid containing and capable of in vivo expression of a rabies glycoprotein gene.

In another aspect, various methods of treatment are provided. For example, the disclosure provides a method of treating a bovine against infection caused by bacteria comprising administering to the bovine animal vaccine compositions comprising a PAA polymer having a Mw range from about 350 kDa to about 650 kDa. In particular embodiments, PAA having a Mw of about 450 kDa are exceptionally useful in eliciting in animals, including bovines, protective immune responses.

In an embodiment, the disclosure provides a method of treating a canine or equine against infection caused by influenza comprising administering to the canine or equine a vaccine comprising an avipox or DNA plasmid containing and capable of in vivo expression of an influenza antigen. In particular embodiments, the influenza antigen is an HA gene.

In another embodiment, the disclosure provides a method for treating a canine against infection caused by rabies virus comprising administering to the canine a vaccine composition comprising inactivated rabies glycoprotein and PAA having a Mw from about 350 kDa and 650 kDa.

The invention also provides avian vaccines, including an avian coccidiosis vaccine, for in ovo administration, which may comprise:

an adjuvant that comprises non-crosslinked PAA having an average Mw from about 350 kDa to about 650 kDa; and a protozoan antigen selected from (1) one or more recombinantly expressed proteins; (2) one or more proteins or other macromolecules isolated from said protozoan by conventional means; (3) whole cell extracts or preparations from said protozoan; and (4) inactivated, live or live-precocious coccidians selected from: *Eimeria* (*E.*) *acervulina, E. adenoeides, E. brunetti, E. colchici, E. curvata, E. dispersa, E. duodenalis, E. fraterculae, E. gallopavonis, E. innocua, E. praecox, E. maxima, E. meleagridis, E. meleagrimitis, E. mitis, E. necatrix, E. phasiani, E. procera, E. tenella* and combinations thereof.

In particular embodiments, the PAA has an average Mw of about 450 kDa.

The invention further provides a method of treating a bovine against infection caused by *E. coli* or *M. hyo* comprising administering to the bovine a vaccine composition comprising PAA and *E. coli* or *M. hyo*. The invention necessarily encompasses a method of treating a swine against infection caused by *M. hyo* comprising administering to the swine the vaccine comprising *M. hyo*.

In another embodiment, the immunological or vaccine composition comprises an antigen corresponding to an agent responsible for a feline infection and/or disease state. The antigen may comprises feline immunodeficiency virus (Hy). The invention also provides a method of treating a feline against infection caused by FIV comprising administering to the feline a vaccine comprising an FIV antigen and PAA.

In yet another embodiment, the disclosure provides a vaccine composition comprising a cancer antigen. In a related embodiment, the disclosure provides a method of treating a subject against cancer comprising administering to the subject the vaccine composition comprising the cancer antigen and PAA.

The examples hereafter, with reference to the Figures, highlight the properties and advantages of the polymers used in the invention. In these examples, NaPAA designates the polymer sodium salt, whatever it is according to the invention or not.

When not specified, "molecular weight" means "weight average molecular weight".

Example 1—Materials and Methods for the Caracterization of the Polymers

All the determinations of the Mw, Mark Houwink slope, IP, monomer and persulfates contents were carried out according to the procedures hereafter.

I.1—Determination of Mw, Mark Houwink slope, and IP

1. Chemicals and Reagents

Water was purified on a Milli-Q-UF system (Millipore, Milford, Mass., USA). Phosphate Buffered Saline (PBS 1C; 6.5 mMol·L$^{-1}$ Na$_2$HPO$_4$, 2H$_2$O; 1.5 mMol·L$^{-1}$ KH$_2$PO$_4$; 2.7 mMol·L$^{-1}$ KCl; 137 mMol·L$^{-1}$ NaCl; pH 6.8) was prepared in-house. Determination of gel permeation characteristics was made with DNA (CAS number 73049-39-5) from Sigma Aldrich (Saint Quentin Fallavier, France) and sucrose (CAS number 57-50-1) from VWR (Darmstadt, Germany). Standards used as system calibration were obtained from Malvern (Malvern, UK) for Pullulan 100 KDa and from Agilent (Santa Clara, Calif.) for Pullulan 400 KDa.

2. Size Exclusion Chromatography (SEC) with Triple Detection

A Viscotek GPCmax VE2501 system (Malvern Instrument, Malvern, UK) comprising a HPLC pump with built-in degasser and autosampler with 100 μL injection loop was used to perform the HP-SEC analyses. A Viscotek TDA 302 detector system with refractive index, right angle light scattering and four-capillary differential viscometer detectors was used for on-line SEC signal detection. Detectors were in the following order: LS (right angle light scattering)-RI (refractive index)-VIS (four-capillary differential viscometer). A 0.22 μm nylon pre-filter was placed between the column and detectors. OmniSEC 4.7 software program was used for the acquisition and analysis of SEC data. All the detectors were calibrated with 100 KDa pullulan standard in a mobile phase of PBS 1C. PBS 1C mobile phase was filtered through 0.22 μm Millipore cellulose nitrate filter and degassed before use. Separation of NaPAA samples was achieved through two A6000M (8 mm ID×30 cm L) columns (Malvern) connected in series. Elution was isocratic at a flow rate of 0.6 mL·min$^{-1}$. 100 samples were injected with a targeted NaPAA concentration at approximately 0.4 mg·mL$^{-1}$ for Mw, IP, and Mark Houwink slope measurements. The pullulan 400 kDa standard was used as a "control" sample for all analyses. The column's void volume ($V_0$) and total permeation volume ($V_t$) were determined by injection of high-molecular-weight DNA and sucrose, respectively.

3. Preparation of Standards and Samples

Pullulan, DNA and sucrose standards were prepared by dissolution of raw materials in PBS 1C to final concentrations at 1, 0.1 and 2 mg·mL$^{-1}$ respectively. NaPAA were formulated and diluted at target concentration in PBS 1C.

4. Determination of NaPAA do/Dc Value and Mw, Mark Houwink Slope and IP Measurements.

Dn/dc coefficient is related to molar mass according to the following relationship (Zimm, 1948, J. chem. Phys., 16, 1099-1116):

$$\frac{KC}{R_\theta} = \frac{1}{M_w P(\theta)} + 2A_2 C$$

Where K is the optical constant which includes dn/dc for a particular scattering system described in following equation, C is the concentration of NaPAA in the sample, $R_0$ is the excess intensity of light scattered at angle θ, Mw is the weight-average molecular weight and $A_2$ is the second virial coefficient, which can be taken as zero, owing to the extremely low concentration of the individual sample fractions. P(θ) is the particle scattering function which represents the angular dependency of light scattering intensity, and is related to radius of gyration (Rg) of the polymer molecule.

$$K = \frac{4\pi^2 n_0^2}{N_A \lambda_0^4} \left[\frac{dn}{dc}\right]^2$$

with $n_0$ being the refractive index of the solvent in the sample; $N_A$ the Avogadro's number; $\lambda_0$ the wavelength of the laser beam in vacuum.

For small molecules whose sizes are smaller than $\lambda_0/20$, the intensity of scattered light is assumed to be independent of the scattering angle, so that P(θ)=1 for all angles.

The resulting expression is now:

$$R_0 = KCM_W$$

The dn/dc of NaPAA was automatically calculated by OmniSEC software using increasing known concentrations of NaPAA with SEC-triple detection system from 0.4 to 1 mg·mL$^{-1}$. Each concentration was injected in duplicate. This experiment has been repeated under the same conditions with different representative NaPAA batches of known concentrations. Final dn/dc coefficient corresponded to the mean of these determinations and was determined to be 0.172 mL·g$^{-1}$. This dn/dc value was used for further molecular weight determinations.

The determinations of Mw, IP and Mark Houwink slope were conducted with a solution of the polyacrylic acid polymer salt in PBS 1C, with a known concentration of the polyacrylic acid polymer salt, for instance of 0.4 mg·mL$^{-1}$. As the polyacrylic acid salt represents more than 95% of the dry weight of the polyacrylic acid polymer salt, the weight of the dry matter is considered to be the dry weight of the polyacrylic acid polymer salt.

The intrinsic viscosity (IV) of a NaPAA is related to its molecular weight and conformation; and is represented with the Mark-Houwink diagram:

$$IV = K \cdot MW^a$$

Where "a" and "K" are constants for a given solute-solvent system and "a" exponent varies from 0 (solid sphere) to 2 (rod shape).

The Mark Houwink slope "a" was determined from this formula IV=K·MW$^a$.

A slope "a" superior or equal to 0.7 means that the NaPAA can be considered as linear.

Polydispersity Index (IP) is defined as Mw/$M_n$, Mn being the number average molecular weight. The Mn of NaPAA was automatically calculated by the Omni SEC software.

I.2 Determination of Persulfates and Acrylate Monomers

A. In Raw Materials

1. Chemicals and Reagents

Water was purified on a Milli-Q-UF system (Millipore, Milford, Mass.). 25 mM (phase A) and 200 mM (phase B) sodium hydroxide solutions were prepared with 46-51% concentrated sodium hydroxide from Fisher Scientific (Illkirch, France). 0.1N sodium hydroxide was from VWR (Darmstadt, Germany). Standards used for calibration were obtained from Fisher Scientific (Illkirch, France) for sodium persulfate and from Sigma Aldrich (Saint Quentin Fallavier, France) for sodium acrylate. Internal standard used to correct sample preparation deviation was sodium oxalate from Sigma Aldrich (Saint Quentin Fallavier, France).

2. High Performance Anion Exchange Chromatography with Conductimetric Detection

Acrylate and persulfate impurities in NaPAA samples were analyzed simultaneously by High Performance Anion Exchange Chromatography (HPAEC) with conductimetric detection. An ICS-3000 (Dionex, Thermo Fisher Scientific, Pittsburgh, Pa.) ion chromatography system was used. It was equipped with an SP-1 pump, a thermostated autosampler (5° C.), thermostated column (40° C.) and a conductimetric detector compartment (30° C.). An ATC3 RFIC (9×24 mm) carbonate trap column (Thermo Fisher Scientific) was positioned in front of the column to capture water carbonate anions and improve global analytical sensitivity. Analytical separation was achieved on an anion exchange AS-11HC column (250×4 mm) from Dionex (Thermo Fisher Scientific) with a gradient elution from 25 mM (phase A) to 200 mM (phase B) sodium hydroxide solution. The gradient program was: 0% B (12 min), 0-40% B (5 min), 40-100% B (8 min), 100% B (25 min), 100-0% B (1 min), 0% B (9 min). The flow rate of the mobile phase was 1 mL/min and the injection volume was 50 μL. An AG-11HC pre-column (50×4 mm) from Dionex (Thermo Fisher Scientific) was used to protect the analytical column. A Dionex conductivity suppressor (AERS 082540, Thermo Fisher Scientific) was positioned in front of the detector compartment to improve the signal. In these chromatographic conditions, retention times for acrylate, oxalate and persulfate were around 4, 11, and 45 minutes respectively.

3. Preparation of Samples

Before chromatographic analysis, high molecular weight species were removed from the samples. In brief, NaPAA samples were diluted ten-fold with water (leading to a concentration of 10 mg/mL in NaPAA) and sodium oxalate internal standard was added to reach a concentration of 50 μg/mL. Then 500 μl of the samples were centrifuged at 14000 g during 30 minutes through successively a Amicon Ultracel 0.5 ml-100k and a Amicon ultracel 0.5 ml-3k centrifugal filter obtained from Merck Millipore (Darmstadt, Germany). Before use, the Amicon centrifugal filters were washed with water and 0.1N NaOH successively to remove glycerol.

4. Calibration and Results

The quantification of persulfate and acrylate impurities was performed by external calibration prepared with commercial standards. Six concentrations ranging from 1-100 μg/mL sodium acrylate and persulfate were mixed in water and 200 μL of 500 μg/mL sodium oxalate internal standard was added to each concentration. The calibration curve followed a linear model for persulfate, and a quadratic model for acrylate. The impurities contents were expressed in % w/w (% weight of acrylate or persulfate impurity over dry NaPAA weight) or in μg of persulfate or acrylate impurity per gram of raw material NaPAA.

B. In NaPAA Polymers Obtained after Purification

Persulfate and residual acrylic acid impurities in NaPAA samples after the purification step (by dialysis, ultrafiltration or gel filtration) were determined as described above for their determination in the NaPAA raw material samples. However, in the purified samples, the 10 fold dilution step was omitted from the sample preparation procedure. For persulfate, the chromatographic conditions were the same as for the raw material NaPAA and the analysis was managed as a limit test with a 100 ng/mL limit of detection. For acrylate, the same HPAEC system was used but the analytical separation was achieved on an anion exchange CarboPac™ SA10 column (250×4 mm) from Dionex (Thermo Fisher Scientific) with a gradient elution from 30 mM (phase A) to 200 mM (phase B) sodium hydroxide solution. The gradient program was: 0% B (14 min), 0-100% B (6 min), 100% B (15 min), 100-0% B (1 min), 0% B (9 min). The flow rate of the mobile phase was 1 mL/min and injection volume was 50 μL. A CarboPac™ SMOG column (50×4 mm) from Dionex (Thermo Fisher Scientific) was used to protect analytical column. A Dionex conductivity suppressor (AERS 082540, Thermo Fisher Scientific) was positioned in front of detector compartment to improve the signal. In these chromatographic conditions, the retention time for acrylate was around 11 minutes. Residual acrylic acid impurity was determined from a linear calibration curve constructed using an external acrylic acid standard at 20-500 ng/ml in PBS 1C. Results were expressed as above in % w/w (% weight of acrylate or persulfate impurity over dry NaPAA weight) or in μg of persulfate or acrylate impurity per mL of NaPAA adjuvant solution.

Example 2—Tests on Adjuvant Activities

1) Evaluation of the Adjuvant Effect of PAA According to the Invention in Comparison with 2 PAAs of the Prior Art, in Relation with *Staphylococcus aureus* Antigen The adjuvant activity of polymer-based formulations was tested in outbred OF1 mice using the type 5 polysaccharide from *S. aureus* (PS5) conjugated to recombinant exotoxin A from *Pseudomonas aeruginosa* (rEPA) as model antigen.

The antigen was prepared in the following manner:

*Staphylococcus aureus* (Reynolds strain) was grown for 72 hours in SATA-1 broth medium under agitation (100 rpm) and then inactivated by the addition of a 1/1 (v/v) phenol/ethanol solution to a final concentration of 2% w/v. Bacteria cells were sedimented at 16 000 g for 75 min. The cell paste was suspended at 0.5 g (wet weight) per ml in 50 mM Tris-2 mM $MgSO_4$, pH 7.5. Lysostaphin (100 μg/ml) was added and the suspension was incubated at 37° C. for 4 hours under agitation. Subsequently, benzonase was added at a concentration of 5 U/ml and the incubation was continued for 2 more hours. The reaction mixture was concentrated by tangential flow filtration (30 000 Da molecular-weight cut-off). The resulting concentrated material was digested with benzonase (5 U/ml) for 6 hours at 37° C. and then with pronase (at 4 U/ml) at 37° C. for 15 hours in the appropriate buffer (Tris 50 mM at pH 8.0 containing 1 mM $MgCl_2$ and 1 mM $CaCl_2$). After centrifugation at 5 000 g for 30 min, the supernatant was concentrated by tangential flow filtration (30 000 Da MWCO). This solution was then adjusted to a final concentration of 50 mM Tris HCl, pH 7.5. Aliquots were loaded on a Q Sepharose (20 mL) column equilibrated with 50 mM Tris HCl, pH 7.5. The column was eluted at a flow rate of 2 ml/min and fractions of 5 ml were collected. The column was washed with 5 volumes of the starting buffer. The polysaccharides were then eluted with a 250 ml linear gradient of 0 to 0.5 M NaCl in 50 mM Tris HCl, pH 7.5. Fractions containing the polysaccharides and no teichoic acid, as detected by optical absorption at 210 nm and by High-Performance Anion-Exchange Chromatography (HPAEC-PAD), were dialyzed, and freeze-dried.

The purified polysaccharide was then activated in NaCl by adipic acid dihydrazide (ADH). The pH was adjusted to 4.9 and ethyldimethylaminopropylcarbodiimide (EDAC) was added. As the activation, which lasted 90 min at ambient temperature, progressed, the pH was constantly adjusted to a value of 4.9 with 0.1 N HCl. The reaction was stopped by the addition of NaOH up to neutralization (pH 7.0). The activated polysaccharide was then dialyzed against 500 mM NaCl aqueous solution and then against water. The activated and dialyzed polysaccharide was then lyophilized. The percentage functionalization was estimated at about 5.9% (w/w).

A solution of the activated polysaccharide was mixed with the carrier protein (rEPA) in NaCl and EDAC. The conjugation took place at 4° C., with a pH maintained at 5.7 through the addition of 0.1 N HCl. After 90 min, the reaction was stopped by addition of 0.2 N NaOH up to a pH of 7. The conjugated antigen was then dialyzed against a NaCl aqueous solution and then purified by size exclusion chromatography on a sepharose Cl-4B column equilibrated with 200 mM NaCl in a 10 mM phosphate buffer, pH 7.2. The fractions which contained conjugates (as detected by optical absorption at 206 nm and 278 nm) and which are mainly eluted with the dead volume of the column, were combined.

The polymer formulations were prepared in the following manner:

Product named PAA225000 (Ref. 18613, sodium salt) was obtained from Polysciences Europe (Eppelheim, Germany) in the form of a concentrated solution. It has been diluted with water to obtain a concentration of 20 mg/ml, and maintained under agitation at room temperature during 12 hours. The pH has been adjusted to 7.55 with HCl and the solution has been dialyzed at room temperature against 150 mM NaCl aqueous solution (3 consecutive baths) by using 2 kDa cutoff dialysis cassettes (Thermo Fischer Scientific, Courtaboeuf, France). The solution was then filtered through a 0.22 μm PVDF membrane, for sterilization. The Molecular Weight of the polymer salt was then measured and is 488 550 Da. Its Mn was 129 070 Da and its IP 3.8.

The polymer was then stored at +4° C., as a solution comprising 20 mg/ml of polymer in 150 mM NaCl aqueous solution. This solution was then mixed with PBS 1C concentrated 10 times with sterile water, in order to get a saline solution comprising 2 mg/ml of polymer salt.

Product named PAA20 was obtained as a sodium salt from Polymer Expert (Pessac, France) in the form of a dry powder. It was rehydrated in water to the concentration of 20 mg/ml and maintained under agitation at room temperature during 12 hours. The solution was then filtered through a 0.22 μm PVDF membrane, for sterilization. The Molecular Weight of the polymer salt was measured at 100 700 Da. Its Mn was 46 700 Da and its IP 2.2. The polymer was then stored at +4° C., as a solution comprising 20 mg/ml of polymer salt in 150 mM NaCl aqueous solution. This solution was then mixed with PBS 10 C and with sterile water, in order to get a saline solution comprising 2 mg/ml of polymer salt.

CARBOPOL® 974 P (named)CARBOPOL® which is a reticulated PAA polymer, with a Molecular Weight of several millions Da, was diluted with PBS to get a solution comprising 2 mg/ml of polymer.

The adjuvanted formulations to be injected to animals were prepared by vol/vol mixing of the antigen solution and of the polymer solution. Each injected dose had 200 μg of polymer and 2.5 of polysaccharide in PBS 1C solution.

Immunizations:

Groups of 5 to 10 OF1 mice, aged 7 to 9 weeks, were immunized either with PAA20, PAA225000 or CARBOPOL® alone (these were used as negative controls) or with the formulations comprising both the antigen and the adjuvant. One group of mice was injected with PS5-rEPA alone. Doses were administered via the subcutaneous (SC) route in the scapular region on D0, D21 and D35. Blood samples were collected on D42 for immune response analysis.

Blood samples were collected in vacutainer tubes containing a coagulation activator and a serum separator gel (Becton Dickinson, Meylan, France). Tubes were centrifuged at 2600 g for 20 min to separate serum from cells. Sera were transferred into deep-well plates and heat-inactivated at 56° C. for 30 min before storage at −20° C. until their use in subsequent assays.

The test comprised different groups as follows:
PBS
Carbopol®
PAA20
PAA225000
PS5-rEPA
PS5-rEPA+Carbopol®
PS5-rEPA+PAA20
PS5-rEPA+PAA225000

The blood samples were used to test the specific IgG1 and the IgG2a antibodies produced by the immunized mice.

The ELISA test used activated polysaccharide PS5 (PS5 conjugated to ADH: PS5-AH) as antigen for the coating. Briefly, ELISA plates were coated with 100 μL per well of 1 μg/mL of activated polysaccharide solution in PBS 1C. Plates were incubated 12 hours at 4° C. and emptied by plate inverting. Wells were blocked by adding 150 μL of saturation buffer 1 (PBS 1C/Tween 0.05% w/v/Bovine albumin 1% w/v) and incubation for 1 h at 37° C. ELISA plates were emptied by inverting. Two-fold serial dilutions of each serum (12 times) were carried out directly in ELISA plates using buffer 1 as dilution buffer for a final volume of 100 μL per well. Plates were incubated for 90 min at 37° C. and then washed 3 times (250 μL per well) with buffer 2 (PBS 1C/Tween 0.05% w/v). Anti-mouse IgG1 or anti-mouse IgG2a peroxidase conjugate were diluted in buffer 1 (1/8000) and used as secondary antibodies (100 μL per well). After 90 min incubation at 37° C., ELISA plates were washed 3 times with buffer 2 (250 μL per well). The reaction was developed by adding 100 μL of a tetramethylbenzidine substrate solution to each well and stopped after 30 min at room temperature with 100 μL/well of 1 N HCl. Absorbance was measured at 450-650 nm. Antibody titers are expressed in arbitrary units corresponding to reciprocal serum dilution for OD450 nm=1 using SoftmaxPro software.

The results obtained are summarized in the FIG. 1 and show that:

1) No background was measured in negative control sera (<1.3 Log) from mice immunized either with PBS 1C or with polymer-based formulations injected alone (data not shown).
2) A specific immune response against the PS5 polysaccharide, mainly an anti-PS5 IgG1 (4.8 Log), was obtained after the third immunization with PS5-rEPA conjugate alone. The anti-PS5 antibody response elicited by the PS5-rEPA conjugate injected alone was mainly Th2-driven, with an IgG1/IgG2a ratio close to 126.
3) The anti-PS5 IgG1 titers were not increased when PS5-rEPA conjugate was formulated either with Carbopol®, PAA20 or PAA225000, with mean of anti-PS5 titers close to 4.8 Log. The co-injection of Carbopol® or PAA20 elicited an increase of anti-PS5 IgG2a titers but these anti-PS5 antibody responses were still mainly Th2-driven, with IgG1/IgG2a ratios close to 50 and 63, respectively. A strong increase of anti-PS5 IgG2a titers (4.5 Log) was observed when PS5-rEPA conjugate was co-injected with PAA225000. The co-injection of PAA225000 elicited a Th1 biased anti-PS5 antibody response with an IgG1/IgG2a ratio close to 2.

In conclusion, this test demonstrated that while the antigen alone mainly induced a Th2 response, the adjuvant according to the present invention, in comparison with the other tested polymers, was able to induce a much more pronounced Th-1 immune response without affecting the Th-2 response.

The blood samples were also tested for their ability to induce opsonic activity in human peripheral mononuclear cells (hPMNs). For this test, pooled sera from each group were tested in serial ten-fold dilutions using the Lowenstein strain (ATCC 49521) grown for 20 h at 37° C. in TSB medium alone or supplemented (stationary phase).

Human peripheral blood from healthy human volunteers was collected in sodium heparin vacutainers. Ten milliliters per donor were required. Leukocytes were isolated by lysis of red blood cells in ammonium chloride lysis buffer. The cells were washed twice in PBS 1C and finally suspended in 5 mL of OPA medium (RPMI-Hepes supplemented with 0.5% BSA and 2 mM Glutamine). Large leukocytes (mainly hPMNs (95%)) were then counted on the Multisizer Coulter counter and were adjusted to a concentration of $0.25 \times 10^6$/mL in OPA medium.

After 20 h of growth, bacteria were washed twice in PBS 1C and re-suspended in 5 mL PBS 1C. Bacterium concentration was adjusted to $10^8$ CFUs/mL in OPA medium.

An oxidative burst assay was performed in a 96-well polypropylene Deepwell plate. The plate was kept on ice upon sequential addition of the reagents. Reagents were added to the wells in the following order: 50 µL of heat-inactivated specific sera at the determined dilution from 1/10 to 1/640, 250 µL of bacteria, 50 µL of baby rabbit complement at 1/10, 100 µL of leukocytes and 50 of DHR (Molecular Probe, D632) at 1 mg/mL. The final volume of reaction was 500 µL. The plate was then incubated for 25 min at +37° C. under gentle shaking, in the dark. The final bacteria/leukocyte ratio was 100:1, the final dilution of sera and complement ranged from 1/100 to 1/6400 and the final concentration of the DHR was 0.1 mg/mL. At the end of the incubation period, the plate was placed on ice to stop the reaction. Analysis was performed on the Cytomics FC500. The oxidized form of DHR, rhodamine 123, emits a bright fluorescence upon excitation at 488 nm. On a (FSC/SSC) dot plot, a gate was defined on the large granular population of leukocytes to differentiate the PMN population. Three thousand events were acquired from each well on this gate. Results were expressed as the percentage of fluorescent activated PMNs (Rhodamine 123-positive PMNs) among the entire PMN population.

The results are displayed in Table 1 here-under:

TABLE 1

| Antigen | Adjuvant | Lownstein TSB 20 h Oxidative burst [1] |
| --- | --- | --- |
| PS5-rEPA | — | + |
|  | PAA20 | ++ |
|  | PAA225000 | +++ |
|  | Carbopol ® | ++ |

[1] % of activated PMNs/entire PMNs population:
+++ (80%-100% at 1/1000 serum dilution);
++ (80%-100% at 1/100 serum dilution);
+ (30%-70% at 1/100 serum dilution)

These results in Table 1 indicate:
1) No activated PMN was detected with negative control sera from mice immunized with either PBS or with polymer-based formulations injected alone (data not shown).
2) PS5-rEPA conjugate elicited anti-PS5 serum antibodies able to weakly activate hPMNs in presence of bacteria. The percentage of activated hPMNs producing oxidative burst was estimated at 30% to 70% for a 1/100 serum dilution.
3) Co-injection of PS5-rEPA with either Carbopol or PAA20 slightly increased the ability of anti-PS5 serum antibodies to recognize the surface of S. aureus Lowenstein strain. The percentage of activated hPMNs producing oxidative burst was estimated at 80% to 100% for a 1/100 serum dilution.
4) Co-injection of PS5-rEPA with PAA225000 clearly improved (ten-fold increase) the ability of anti-PS5 serum antibodies to recognize the surface of S. aureus Lowenstein strain. The percentage of activated hPMNs producing oxidative burst was estimated at 80% to 100% for a 1/1000 serum dilution.

The sera obtained with PAA225000 and PAA20 or the sera obtained with mice immunized with the antigen alone were also tested for their ability to kill the Staphylococcus aureus Lowenstein bacteria in presence of human PMNs.

For this test, whole blood was collected in sodium citrate bags from healthy human donors by EFS (Etablissement Francais du Sang) and fresh human polymorphonuclear leukocytes (PMNs) were isolated according to the following procedures. Erythrocytes were lysed by incubating 5 mL blood and 45 mL lysis buffer for 10 min at +20° C. PMNs were washed twice in HEPES saline buffer (HBSS w/o CaMg, ref pH7.4). The viability of the PMNs was more than 90%, as shown by trypan blue exclusion. The PMN suspension was diluted to $10^7$ cells per mL.

The Lowenstein S. aureus strain was cultured 12 hours in TSB medium. Bacterial cells were pelleted, washed with OPA medium (RPMI+5% SVF+0.05% Tween 20), and suspended in normal saline to $5 \times 10^7$ cells per mL. The following substances were added into each tube: 0.25 mL PMNs, 50 µL of diluted test serum, 50 µL homologous S. aureus cells (ratio 1 cell/1 bacteria), 50 µL of 0.5% w/v rabbit complement and OPA medium to complete volume at 500 µL/well. Control tubes with S. aureus in the presence of PMNs, test serum, or complement alone were included in the assay. Assay tubes were incubated for 1 hour at +37° C. with shaking. Dilutions were performed in 3-steps (3*1/15 dilutions) and 50 µL of the different dilutions were dropped six times in TSA gelose and incubated during 12 hours. The percentage of bacterial survival was defined at each dilution point, if possible, using the formula: (number of viable bacterial/original inoculum)×100.

The data obtained in 2 independent analyses are displayed in Table 2 (ONS=Nonspecific opsonophagocytosis) below:

TABLE 2

|  | Test 1 | | Test 2 | |
| --- | --- | --- | --- | --- |
|  | Vs ONS | | | |
|  | ONS: 7% | | ONS: 14% | |
| Dilution of pool of sera Anti-PS5 sera | 1/100 | 1/500 | 1/100 | 1/500 |
| PS5-rEPA | 39 | 9 | 38 | 19 |
| PS5-rEPA + PAA20 | 31 | 2 | 26 | 10 |
| PS5-rEPA + PAA225000 | 50 | 23 | 42 | 18 |

These results displayed in Table 2 show that:
1) No bacterium killing was detected with negative control sera from mice immunized with either PBS or with polymer-based formulations injected alone (data not shown).
2) PS5-rEPA conjugate elicited anti-PS5 serum antibodies displaying a weak killing activity in presence of hPMNs with a bacterial killing percentage of 39% at 1/100 serum dilution. Bacterial killing activity was not more measured when pool of sera was diluted to 1/500.
3) Co-injection of PS5-rEPA with PAA20 did not improve the ability of anti-PS5 serum antibodies to kill of S. aureus Lowenstein strain.
4) The adjuvant effect of PAA225000 on bacterium killing was observed in the test 1, with a bacterial killing percentage of 50% vs 39% for the non-adjuvanted PS5-rEPA at 1/100 serum dilution and a bacterial killing percentage of 23% vs 9% for the non-adjuvanted PS5-rEPA at 1/500 serum dilution.

The general conclusion of this test in relation with *Staphylococcus* antigen, is that the adjuvant of the present invention showed superior efficacy as compared with adjuvants having a lower Molecular weight.

2) Testing the Adjuvant Effect of Different Polymers on the Immune Response Induced by hCMV-gB The aim of this study was to evaluate the impact of the Molecular Weight of the polyacrylic acid (PAA) polymer on the adjuvant effect. This has been done by using as a model antigen a recombinant protein which derives from the gB glycoprotein of the human cytomegalovirus (hCMV-gB).

This recombinant protein was produced by a recombinant CHO line transfected with a plasmid called 0708985pEE14.4, which contains a modified gB gene. To facilitate the production of this recombinant protein by the CHO line, the gB gene, the sequence of which is described in U.S. Pat. No. 5,834,307, was modified beforehand by deleting the part of the gene which encodes the transmembrane region of the gB protein corresponding to the amino acid sequence between valine 677 and arginine 752 and introducing 3 point mutations at the cleavage site. The protein produced by the CHO line, called gBdTM, corresponds to a truncated gB protein depleted of the cleavage site and of the transmembrane region.

The gBdTM protein produced in the culture medium was subsequently purified by chromatography and stored in the form of a stock solution containing >0.2 mg/ml of gBdTM in phosphate buffer.

The PAA with different molecular weights were as follows:

PAA20 and PAA225000 as described and prepared in the paragraph "1) Evaluation of the adjuvant effect of PAA according to the invention in comparison with 2 PAAs of the prior art, in relation with *Staphylococcus aureus* antigen".

PAA3000 (Ref. 06568), PAA6000 (Ref 06567), PAA50000 (Ref. 00627) and PAA60000 (Ref. 18611) are NaPAA and were provided by Polysciences in the form of dry powder (for PAA6000) or concentrated solutions for the others.

PAA20 was mixed with water to the concentration of 20 mg/ml and maintained under stirring at room temperature during 12 hours. The solution was then filtered through a 0.22 µm PVDF membrane and kept stored at +4° C., as a solution comprising 20 mg/ml of polymer in 150 mM NaCl aqueous solution. This solution was then mixed with PBS 10C and sterile water, in order to get a saline solution comprising 2 mg/ml of polymer.

The PAAs from Polysciences were diluted with sterile water to a concentration of 20 mg/ml, adjusted to pH around 7.4 (with the exception of PAA60000 which was not pH adjusted) with NaOH or HCl and dialyzed against 150 mM NaCl (3 consecutive baths) by using a 2 kDa cut-off dialysis cassettes (Thermo Fischer Scientific, Courtaboeuf, France). The solutions were then filtered through a 0.22 µm PVDF membrane, for sterilization. The Mw, Mn and IP were determined and the polymers were stored at +4° C., as a solution comprising 20 mg/ml of polymer salt in 150 mM NaCl aqueous solution.

The Molecular weights (Mw and Mn) and PI of the polymers are indicated in the Table 3 below:

TABLE 3

|  | Mw in Da | Mn in Da | Polydispersity index |
| --- | --- | --- | --- |
| PAA3000 | Non Determined | Non Determined | Non Determined |
| PAA6000 | 9 050 | 2 940 | 3.1 |
| PAA50000 | 133 460 | 56 360 | 2.4 |
| PAA60000 | 133 760 | 44 500 | 3.0 |
| PAA20 | 100 700 | 46 700 | 2.2 |
| PAA225000 | 488 550 | 129 070 | 3.8 |

A squalene emulsion containing the same components as the MF59® squalene emulsion of Novartis was prepared by microfluidisation in order to compare the adjuvant activity of the different polymers to that of prior art adjuvant used as a reference.

The adjuvanted formulations were prepared by vol/vol mixing of the antigen solution with the adjuvant solution.

The adjuvant quantity was 200 µg of polymer per injected dose, or in the case of the emulsion, the final vaccine dose comprised 2.5% v/v of squalene.

The different formulations tested were as follows (gB corresponds to hCMV-gB:2 µg in each formulation)
gB alone,
gB+squalene emulsion,
gB+PAA3000,
gB+PAA6000,
gB+PAA50000,
gB+PAA60000,
gB+PAA20 (PBS)
gB+PAA225000

C57BL/6 mice (8-10 per group) were immunized twice, at Day 0 and Day 28, with the recombinant hCMV-gB antigen (2 µg/injection) combined or not with adjuvant by the IM route (left quadriceps under a final volume of 50 µl). The test included, as a control, a group immunized with hCMV-gB antigen alone.

Blood samples were taken under anesthesia from the submandibular vein at D28 (intermediate bleeding) and after exsanguination by carotid section at D41 from all the animals. Anesthesia was performed by Imalgéne (1.6 mg of Ketamine) and Rompun (0.32 mg of Xylazine) administered under a volume of 150 µL by intraperitoneal route (IP).

For the humoral response assays at D28, 200 µL of blood were collected in vials containing clot activator and serum separator (Becton Dickinson Microtainer SST, ref 365951). After a night at +4° C., blood was centrifuged at 10 000 rpm during 5 minutes and serum was collected and stored at −20° C. until analysis. At D41, 1 mL of blood was collected in vials containing clot activator and serum separator (BD Vacutainer SST ref 367783). After 12 hours at +4° C., the blood was centrifuged at 3000 rpm during 20 minutes and the serum was collected and stored at −20° C. until analysis.

For cellular response assays at D41, spleens were collected in sterile conditions from 5 mice per group. Splenocytes were isolated as follows: freshly collected spleens were dissociated with Gentlemax dissociator (Miltenyi Biotec), cell suspensions were passed through a cell strainer and washed with RPMI medium. Red blood cells were lysed using Red Blood Cell Lysing Buffer (Sigma). After washing, splenocytes were counted and immediately used for the cellular assays.

Seroneutralisation assays:

This technique was used to titrate the functional neutralizing antibodies present in the sera of hCMV-gB immunized animals. Based on the ability of the Cytomegalovirus to infect MRC5 fibroblasts and ARPE-19 cells (human epithelial cells), a serum containing specific functional antibodies against HCMV-gB can inhibit the viral infection of the cells.

a. SN50 on MRC5

Briefly, $1 \times 10^4$ MRC-5 fibroblasts were cultured in 96-well flat bottom plates in DMEM 1% FBS for 1 day in a 5% $CO_2$ cell culture incubator at 37° C. Heat-inactivated sera from immunized animals were serially diluted with 1% FBS (fetal bovine serum) in DMEM (Dulbecco's Modified Eagle's Medium) supplemented with 10% of baby rabbit complement and incubated vol/vol with 3.3 log CCID50 (cell culture infective dose 50%)/ml of hCMV Towne strain for 1 hour in the cell culture incubator. The serum/virus mixtures were then transferred onto the MRC-5 cell monolayers. After 7 days of incubation, culture supernatants were removed and cells were washed four times with PBS 1C and then fixed with 100 µl of 85% acetone in water for 15 min at −20° C. The plates were washed three times with PBS 1C and air dried. Infected cells were detected with a colorimetric reaction. A mixture of two specific hCMV biotinylated-antibodies (anti-IE1 CH160 and anti-gB CH177 HCMV proteins) was added to the wells at 0.5 µg/ml for 1 hour at room temperature. Plates were washed in PBS 1C/0.05% Tween 20 (PBST) before addition of phosphatase alkaline streptavidin for 1 hour at room temperature (22° C.). Plates were washed in PBST and stained with 100 µl of chromogen NBT/BCIP for 30 minutes in the dark at room temperature. After washing, plates were air dried and scanned using a colorimetric ELISPOT plate reader (Microvision Instruments, Evry, France). Dark stained nuclei representative of the cytopathic effect were observed in each well. The serum dilution is considered as neutralizing if no dark focus is observed in the corresponding well. Each dilution of serum was tested on 4 replicates. For each dilution the 50% neutralization (SN50) is calculated by last square regression. The SN50 value (in log 10) is defined as the reciprocal of the highest serum dilution which reduces the number of infected well by 50%. Mean neutralizing antibody titers were calculated for each group of mice.

b. µPRNT50 on ARPE-19

Briefly, $2.5 \times 10^4$ ARPE-19 cells were dispensed in 96-well dark plates the day before the microneutralization (MN) assay. On D0, sera were heat-inactivated at 56° C. for 30 min. Serum samples were serially two-fold diluted in DMEM/F12 1% FBS, starting from 1/10 to 1/10240 in a 96-deep-well plate and incubated with 4.2 log FFU/ml of the BADrUL131-Y4 HCMV virus strain for 60 min at 37° C. in a 5% CO2 cell culture incubator. The serum/virus mixtures were then transferred onto the ARPE-19 cells and incubated at 37° C. in a 5% CO2 cell culture incubator for 4 days.

On D4, after removal of the culture supernatant, cells were fixed with 100 µl of 1% formol in PBS 1C for 1 hour at room temperature. The plates were then washed three times with PBS 1C and air-dried at room temperature before analysis on the Microvision fluorescent plate reader to count infected cells in each well.

As control, two wells of cell control (without virus) and six wells with cells infected with half of the viral dilution containing the 4.2 log FFU/mL were present on each plate. The mean of these six wells defined the threshold of seroneutralization, determined as 50% of the specific-signal value.

Neutralizing end-point titers were defined as the reciprocal of the last dilution that fell below the calculated 50% specific-signal value. Neutralizing titers (µPRNT50) were defined for each individual serum as the last dilution that induced 50% reduction of infected cells, i.e. the last dilution that induced less cell infection than the calculated 50% specific-signal value. Geometric mean neutralizing antibody titers were calculated for each group.

Figure 2:
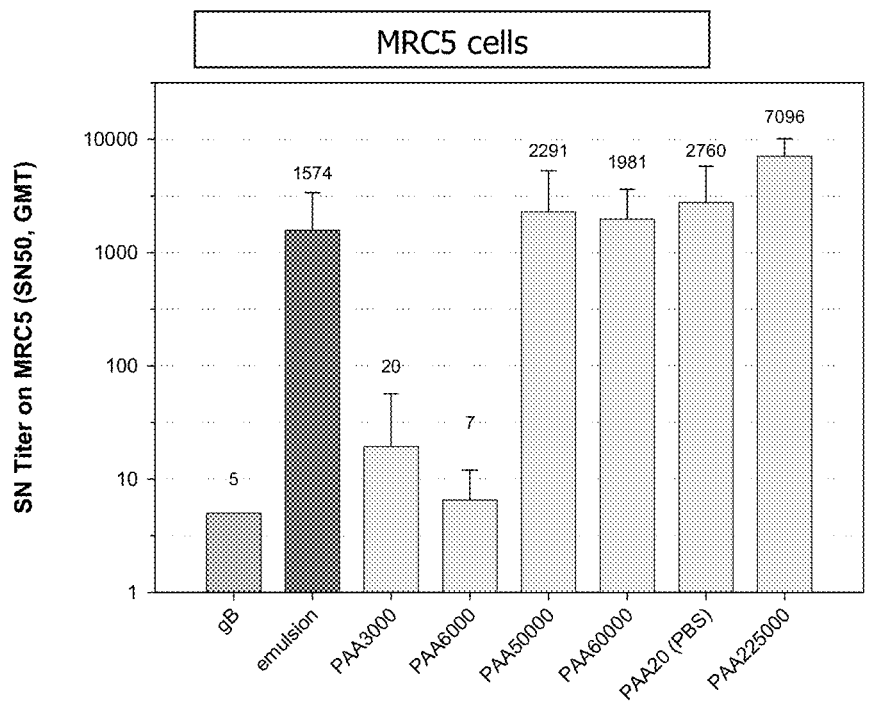
FIG. 2 is a is a graph showing the Geometric mean neutralizing antibody titer (GMT) of sera of groups of C57BL/6 mice immunized with 2 µg of hCMV-gB and squalene emulsion, PAA3000, PAA6000, PAA50000, PAA60000, PAA20 or PAA225000, as measured on MRC5 fibroblasts.
Figure 3:
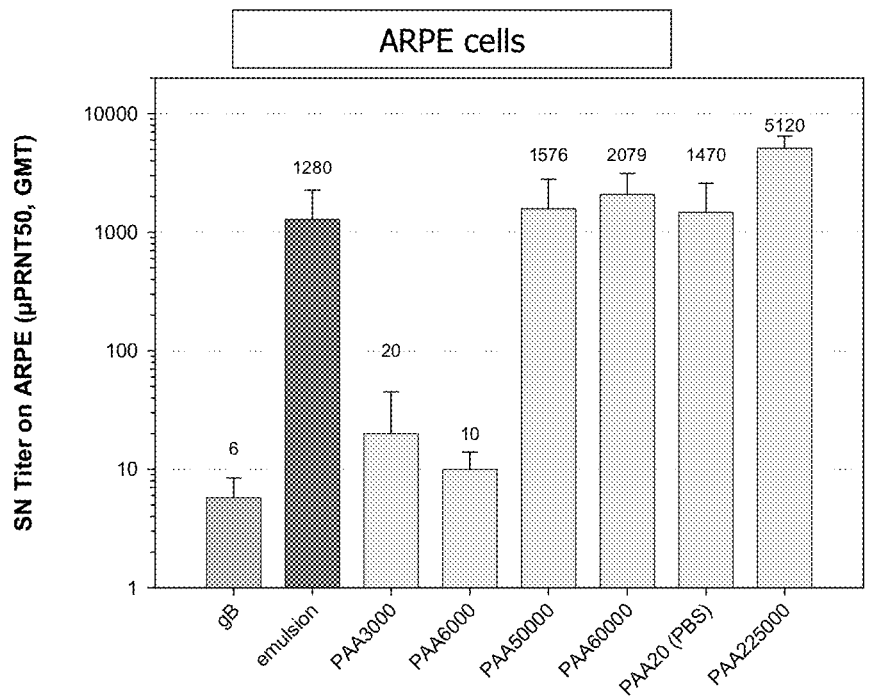
FIG. 3 is a graph showing the GMT for the groups of FIG. 2, as determined by seroneutralization on ARPE-19 cells (human epithelial cells)

The GMT (Geometric mean neutralizing antibody titer) results obtained for each group of immunized mice are displayed in FIGS. 2 and 3:

Similar profiles were observed with both seroneutralization assays on MRC5 fibroblasts and ARPE epithelial cells, whatever the group analyzed. No or low neutralizing antibody titers were detected in mice immunized with unadjuvanted hCMV-gB (GMT=6).

The polyacrylic acid polymer of the present invention gave, by far, the best response.

IgG1 and IgG2c Antibody Responses

Serum IgG1 and IgG2c antibodies directed against hCMV-gB antigen were titrated by a robot ELISA assay according to the following procedure.

Dynex 96-well microplates were coated during 12 hours at 4° C. with 1 µg/well of hCMV-gB, in 0.05 M carbonate/bicarbonate buffer, pH 9.6 (Sigma). Plates were then blocked 1 hour at 37° C. with 150 µL/well of PBS Tween-milk (PBS pH7.1, 0.05 Tween 20, 1% (w/v) powdered skim milk (DIFCO)). All next incubations were carried out in a final volume of 100 µL, followed by 3 washings with PBS pH 7.1, 0.05 Tween 20. Serial two-fold dilution of serum samples were performed in PBS-Tween-milk (starting from 1/100 or 1/1000) and were added to the wells. Plates were incubated for 90 min at 37° C. After washings, anti-mouse IgG1 or IgG2c peroxidase conjugate (Southern Biotech) diluted in PBS-Tween-milk at 1/2000 was added to the wells and plates were incubated for 90 min at 37° C. Plates were further washed and incubated in the dark for 30 min at 20° C. with 100 µL/well of a ready-to-use Tetra Methyl Benzidine (TMB) substrate solution (TEBU). The reaction was stopped with 100 µL/well of HCl 1M (Prolabo). Optical density (OD) was measured at 450 nm-650 nm with a plate reader (Spectra Max—Molecular Devices). The IgG antibodies titers were calculated using the CodUnit software, for the OD value range of 0.2 to 3.0 from the titration curve (reference mouse hyper immune serum put on each plate). The IgG titer of this reference, expressed in arbitrary ELISA units (EU) corresponded to the log 10 of the reciprocal dilution giving an OD of 1.0. The threshold of antibody detection was 10 ELISA units (1.0 log 10). All final titers were expressed in log 10 (Log).

Figure 4:
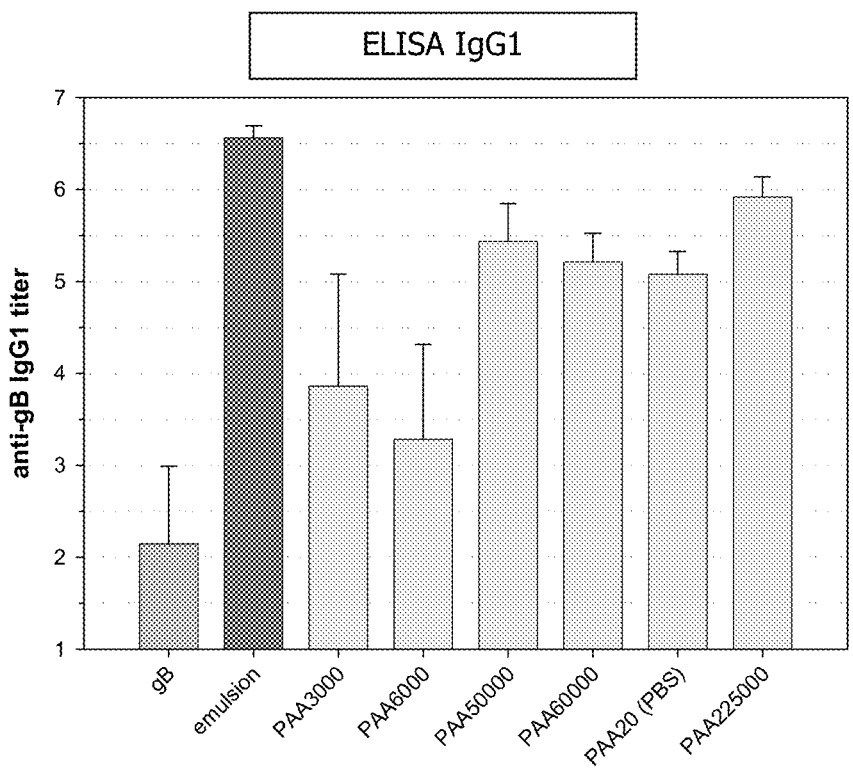
FIG. 4 is a graph showing serum IgG1 antibodies directed against hCMV-gB antigen for the groups of FIG. 2, as determined by ELISA.
Figure 5:
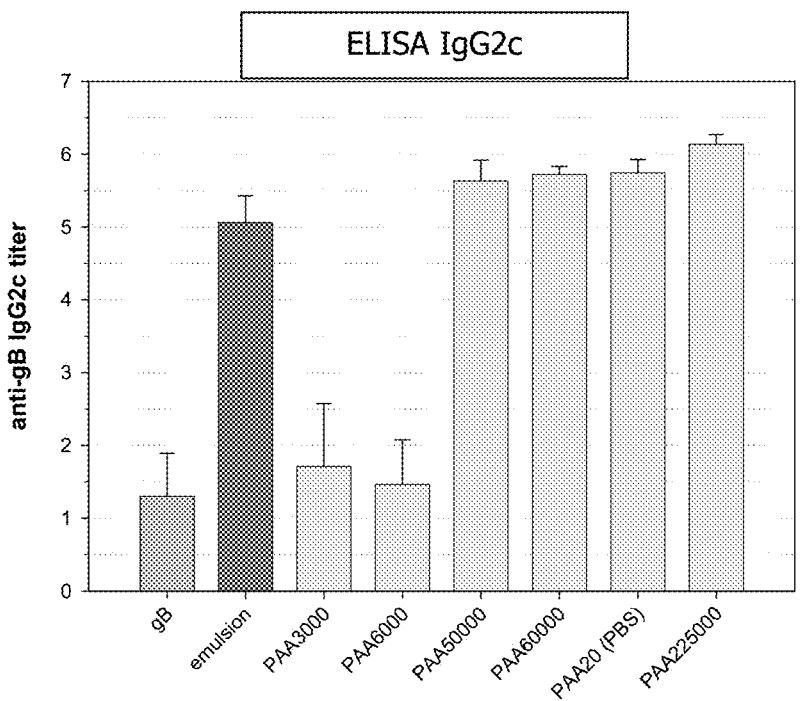
FIG. 5 is a graph showing serum IgG2c antibodies directed against hCMV-gB antigen for the groups of FIG. 2, as determined by ELISA.

The results are depicted in the FIGS. 4 and 5:

These results show that the adjuvanted hCMV-gB antigen induced increased immune responses compared to the unadjuvanted antigen, both for IgG1 and for IgG2c titers, with the exception of the PAA3000 and PAA6000 which have the lowest Molecular Weight. It is interesting to note that the PAA of the present invention is particularly efficient in increasing the immune response of the T helper1 type (Th1), as the IgG2c titers are particularly strong in mice immunized with hCMV-gB combined with PAA of the present invention.

Cytokines Measurements:

Splenocytes from immunized mice were isolated immediately after sacrifice at day 41, plated at $2.5 \times 10^5$ cells per well in 96-well plates and incubated with hCMV-gB (5 µg/well), concanavalin A (0.25 µg/well; positive control) or medium alone (RPMI-GSPβ-10% FCS; background). After 6 days of incubation, the secretion of the IL5 and IFNγ cytokines was measured using the CBA Flex set Kit. Results are expressed as cytokine concentrations in pg/ml (geometric mean per group). Threshold for positive cytokine detection was 5 pg/ml for IL-5 and 2.5 pg/ml for IFNγ.

Figure 6:
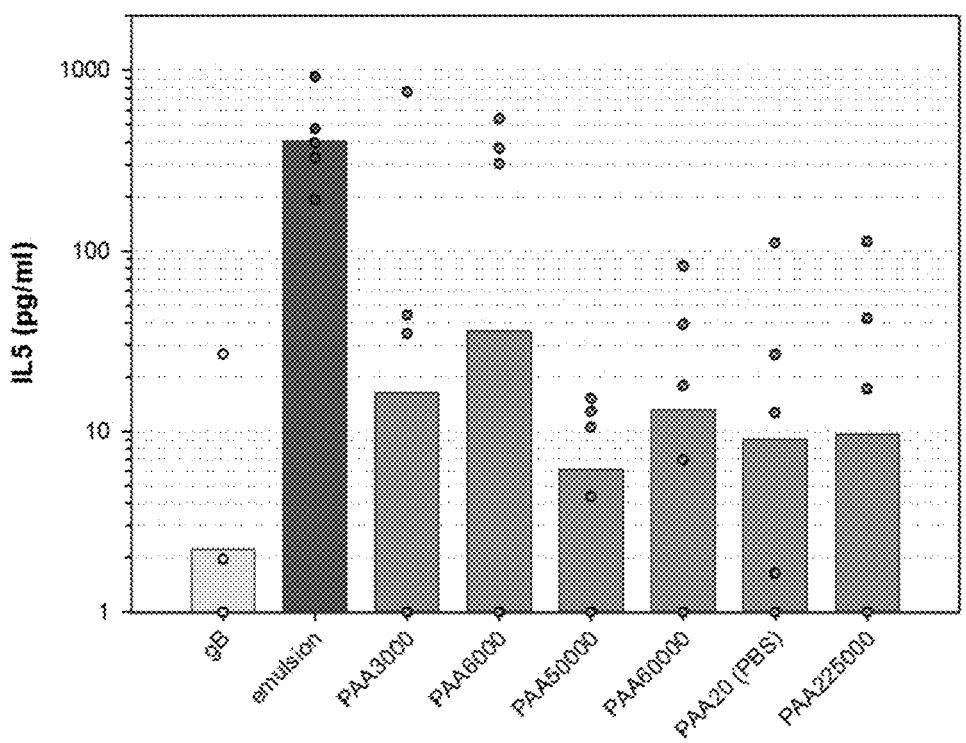
FIG. 6 is a graph showing IL5 cytokine levels for the groups of FIG. 2, as measured using the CBA Flex set Kit.
Figure 7:
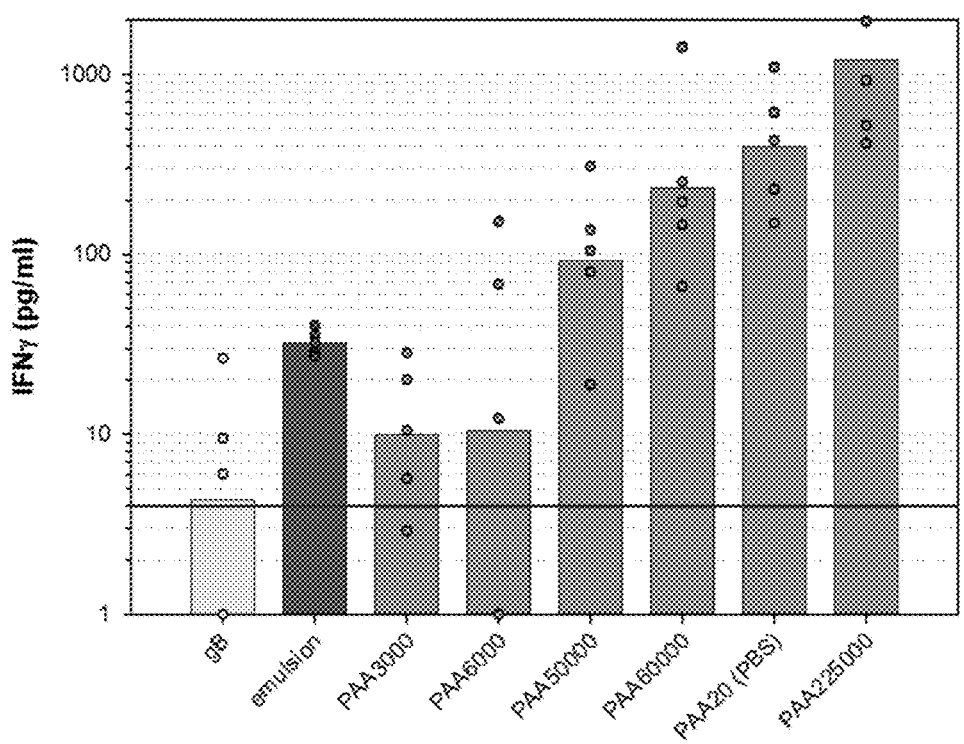
FIG. 7 is a graph showing IFNγ cytokine levels for the groups of FIG. 2, as measured using the CBA Flex set Kit.

The results are displayed in the FIGS. 6 and 7:

These results show that with the emulsion adjuvant, the level of IL5 is high while the level of IFNγ is low. Interestingly, the polyacrylic acid adjuvant according to the present invention induces a low level of IL5 but a high level of IFNγ, which is an indication of an immune response biased towards the Th1 type. This result is in accordance with the immunoglobulin subtyping result.

3) Comparison of a Diafiltered PAA According to the Invention with its Raw Material Before Diafiltration.

In this test, it was shown that the diafiltration did not impact the adjuvant properties of the polymer.

Different formulations were tested comprising the hCMV-gB antigen at 0.08 mg/mL, which was obtained as described in paragraph "2) Testing the adjuvant effect of different polymers on the immune response induced by hCMV-gB".

From a sodium salt of Polyacrylic Acid Polymer provided by Polysciences, two different processes (non-diafiltered preparation and diafiltered preparation) were applied.

For the non-diafiltered preparation, the product obtained from Polysciences was simply diluted with PBS and sterile-filtered through a 0.2 μm cut-off membrane. The concentration of the PAA salt was 17.4 mg/mL. The Mw, IP, and Mark Houwink slope were determined.

For the diafiltered formulation, the product obtained from Polysciences was treated according to the following protocol:
 a) mixing the aqueous solution provided by Polysciences with PBS 1C pH 7.4 under stirring during 15 minutes in order to get a PBS solution comprising 14 mg/ml of polymer,
 b) diafiltering the solution obtained in step a) against 5 volumes of PBS, with a membrane having a cut-off of 50 kDa,
 c) filtering the product obtained in step b) on a 0.2 μm sterilizing filter.

The obtained solution contained 15.9 mg/mL of the PAA salt with a pH of 7.3. The Mw, IP and Mark Houwink slope were determined.

The obtained Mw, IP and Mark Houwink slope obtained before and after diafiltration are presented in Table 4.

TABLE 4

| NaPAA | Mw (Da) | IP | Mark Houwink slope |
| --- | --- | --- | --- |
| diafiltered | 522,030 | 1.6 | 0.9 |
| non-diafiltered | 433,417 | 2.6 | 0.9 |

The Molecular weights Mw and the IP of the polymer before and after diafiltration are consistent with the fact that the monomers and the small oligomers, in particular those less than 2000 Daltons have been eliminated by the diafiltration step.

It is also important to notice that the Mw announced by Polysciences which was determined by GPC (Gel Permeation Chromatography) was 887,000 Da, which is very far from the measured one before diafiltration.

From these two different preparations, immunization formulations were prepared by mixing one of the polymer preparations with the gB solution in the proper ratio, in order to get doses of 50 μl which each contained 2 μg of gB and:
 either 25, 50, 100 or 200 μg of polymer salt from the diafiltered formulation,
 or 25, 50, 100 or 200 μg of polymer salt from the non-diafiltered formulation.

C57BL/6J mice, aged 7 weeks, were immunized twice by the intra-muscular route at Day 0 and Day 21, by one of the prepared formulations. Each preparation was tested in a group of 5 mice. As a control, one group of 5 mice received the antigen alone.

The cellular (IFNγ and IL5) and the humoral responses (IgG antibody subclasses, seroneutralizing antibodies) of immunized mice were monitored 2 weeks after the last immunization (on Day 35) in the same way as described in paragraph "2) Testing the adjuvant effect of different polymers on the immune response induced by hCMV-gB".

The results showed that, as in the preceding test, the adjuvant according to the present invention induced strong Th-1 immune responses accompanied with the induction of strong virus neutralizing antibody titers, and that there was no significant difference between the mice immunized with a diafiltered formulation and the mice immunized with a non-diafiltered formulation.

4) Stability Study of a Diafiltered PAA in Comparison with a PAA Raw Material

In order to check the stability of PAA adjuvants according to the invention, a study has been performed which analyses the variations of the Molecular weight of the polymer salt in accelerated aging tests.

For this test, non-diafiltered preparation and diafiltered preparation were used. The purification was carried out by diafiltration with a membrane of a 50 kDa cut off, and the resulting diafiltered preparation contained 8 mg/mL of a PAA polymer salt having a Molecular weight of 443553 Da in PBS 1C.

Its content in Sodium Persulfate was less than 0.0007% (w/w) of the dry polymer; the content of sodium acrylate was determined to be 0.0011% of the dry polymer.

This preparation was filled in glass vials and maintained either at +5° C., +25° C. or +37° C.

The analyses were performed over 24 months at 5° C., 9 months at 25° C. and 3 months at 37° C. The results obtained during this stability study are displayed in the Table 5 below:

TABLE 5

| T° | Time | Mw (Da) | IP | Mark Houwink slope |
| --- | --- | --- | --- | --- |
|  | T0 | 443 553 | 2.2 | 0.8 |
| 5° C. | 3 M + 5° C. | 451 035 | 2.6 | 0.8 |
|  | 6 M + 5° C. | 456 211 | 2.4 | 0.8 |
|  | 9 M + 5° C. | 463 731 | 2.4 | 0.8 |
|  | 12 M + 5° C. | 441 474 | 2.3 | 0.8 |
|  | 18 M + 5° C. | 433 764 | 2.3 | 0.8 |
|  | 24 M + 5° C. | 443 544 | 2.3 | 0.8 |
| 25° C. | 1 M + 25° C. | 442 254 | 2.3 | 0.8 |
|  | 3 M + 25° C. | 420 513 | 2.5 | 0.8 |
|  | 6 M + 25° C. | 454 505 | 2.2 | 0.8 |
|  | 9 M + 25° C. | 463 731 | 2.4 | 0.8 |
| 37° C. | 1 M + 37° C. | 443 437 | 2.1 | 0.8 |
|  | 2 M + 37° C. | 419 315 | 2.3 | 0.9 |
|  | 3 M + 37° C. | 435 771 | 2.3 | 0.8 |

These results show that there was no significant decrease of the Mw after storage at 5° C. during 24 months, after storage at 25° C. during 9 months and after storage at 37° C. during 3 months, and the Polydispersity Index of the polymer remained the same.

This is in contrast with the results obtained with a composition corresponding to an aqueous solution comprising 10% w/w of comparable PAA salt which has not been dialysed, and which contained sodium persulfate at a concentration of 0.42% w/w with respect to dry weight composition. The initial Mw of the polymer salt was determined at 470,269 Da, whereas the Mw announced by the supplier determined by GPC was 351,100 Da.

The results obtained during the stability study for this non-dialysed polymer solution are displayed in the Table 6 below, and show that the Molecular weight decreases with the time in particular after storage at 25° C. and 37° C.

TABLE 6

| T° | Time | Mw (Da) | IP | Mark Houwink slope |
|---|---|---|---|---|
| | T0 | 470 269 | 4.3 | 0.8 |
| 5° C. | 3 M + 5° C. | 466 916 | 4.8 | 0.8 |
| | 6 M + 5° C. | 486 470 | 5.2 | 0.8 |
| | 9 M + 5° C. | 475 430 | 4.6 | 0.8 |
| | 12 M + 5° C. | 458 407 | 4.8 | 0.8 |
| | 18 M + 5° C. | 449 561 | 3.9 | 0.8 |
| 25° C. | 1 M + 25° C. | 398 694 | 4.0 | 0.8 |
| | 3 M + 25° C. | 345 603 | 4.1 | 0.8 |
| | 6 M + 25° C. | 336 632 | 5.8 | 0.8 |
| 37° C. | 1 M + 37° C. | 310 019 | 4.0 | 0.8 |
| | 3 M + 37° C. | 302 438 | 3.9 | 0.8 |
| | 6 M + 37° C. | 321 482 | 4.2 | 0.8 |

5) Test Showing the Detrimental Effect of Persulfate Content

A sodium salt of Polyacrylic Acid Polymer (provided by Polysciences) was sterilized in an autoclave at a temperature of 121° C. during 15 minutes. The concentration of the PAA salt in the solution was 101.8 mg/g. The Table 7 hereafter shows the Mw, IV (Intrinsic viscosity) and Mark Houwink slope of the PAA salt after and before autoclaving.

TABLE 7

| NaPAA | Mw (Da) | IV (dl/g) | Mark Houwink slope |
|---|---|---|---|
| before autoclaving | 404 784 | 3.5 | 0.9 |
| after autoclaving | 188 782 | 1.9 | 0.9 |

It appears that the treatment in the autoclave led to a drastic decrease of the Mw and IV. A subsequent study was carried out for studying the parameters that can be responsible for this degradation of the polymers under heating. This study showed that the purification of the polymer salt, in particular by diafiltration, was able to stabilize the polymer upon sterilization by autoclaving.

A mixture of NaPAA polymer and persulfate was exposed to heat, in order to reproduce the conditions of autoclaving: the composition was characterized for NaPAA Mw and persulfate content prior and after incubation at 120° C. during 15 minutes. Table 8 details the composition characteristics in terms of NaPAA Mw and persulfate content.

TABLE 8

| PAA | Mw (Da) | IV (dl/g) | Persulfate content % w/w on dry weight |
|---|---|---|---|
| PAA before heat exposure | 434 725 | 1.6 | <0.0005 |
| PAA after heat exposure | 428 672 | 1.6 | <0.0005 |
| PAA + 150 ppm of sodium persulfate) before heat exposure | 428 477 | 1.6 | 0.07 |
| PAA + 150 ppm persulfate after heat exposure | 323 160 | 1.4 | 0.07 |

These results show that the presence of persulfates led to a decrease of Mw, after heat treatment. On the contrary, a PAA with a very weak content of persulfates had a very stable Mw. In conclusion, the heat-stability of a PAA solution could be directly linked to its persulfate content. The diafiltration step introduced in the process of the present invention, removed persulfate impurities from the PAA solutions and afforded heat-stable PAA solutions compatible with sterilization by autoclaving.

Example 3—PAA Supports a Strong Response and Decreases Antigen Payload

Demand for broader protection against livestock pathogens necessitates the addition of antigens to existing vaccine formulations (e.g. the SINTOXAN® products, which generally comprise inactivated toxins and/or bacterins plus aluminum hydroxide adjuvant), or the formulation of separate single-antigen vaccines. Since providing combination vaccines is commercially more desirable, Applicants reasoned that they could add the new antigens while still maintaining the existing dose volume, provided that they could identify a more potent adjuvant with a good safety profile.

Importantly, as the person skilled in the vaccine and immunological arts knows well, one cannot predict ahead of time whether or not a molecular species will function as a safe and effective immunogenic adjuvant. Moreover, even after adjuvant properties have been established a new molecule, because of unpredictable nature of these arts, a skilled person cannot reasonably expect success in applying the new adjuvant to different situations. Variables that impact whether or not a new formulation will function as a safe and protective vaccine include, but are not limited to: 1) adjuvant type/presence; 2) antigen type/nature (peptide, nucleic acid, killed virus, bacterin, etc.); 3) route of administration; 4) target pathogen type/strain; and 5) target species to be vaccinated. Accordingly, the safety and efficacy of a new vaccine adjuvant must be demonstrated across at least several combinations of these variables before any meaningful conclusions as to its general applicability can be drawn.

For the instant case, where the antigen type largely comprised inactivated bacteria, the Applicants reasoned that the ultimate new, more potent and dose-sparing adjuvant would have to be lipase-resistant. Unfortunately, compounds that enable a formulation to be lipase-resistant often can lead to undesirable administration site reactions. As such, a good balance between vaccine safety, efficacy and stability needed to be struck.

Experimental SINTOXAN® vaccines (Merial Brazil—*C. perfringens* B/C; *C. perfringens* D; *C. septicum; C. novyi; C. tetani*) were prepared and tested on mice, guinea pigs and rabbits. As an example, the guinea pig study design and results are presented in Tables 9 and 10, respectively.

TABLE 9

Dose sparing approach using the PAA225000 polyacrylic acid adjuvant

| | (% of standard vaccine) | Antigen Pre-adsorption on aluminum hydroxide | Dose PAA (mg/dose) |
|---|---|---|---|
| Base Vaccine | 1 | Yes | 0 |
| A | 0.2 | Yes | 1 |
| B | 0.2 | Yes | 2 |
| C | 0.2 | Yes | 3 |
| D | 0.2 | Yes | 4 |
| E | 0.2 | No | 4 |

TABLE 10

Summary of efficacy of the dose-sparing immunogenic formulations

| | Tetani | Novyi | Beta | Epsilon | Septicum | Sordellii | Chauvoei | Haemoliticum | pH | Free formol (mg/ml) | $Al^{3+}$ (mg/ml) | Sterility | Safety |
|---|---|---|---|---|---|---|---|---|---|---|---|---|---|
| Specific | * ≥2.5 UI/mL | * ≥3.5 UI/mL | ** ≥10 UI/mL | ** ≥2 UI/mL | *≥2.5 UI/mL | ** ≥1 UI/mL | ** ≥87.5% | ** ≥87.5% | 6.5 a 7.5 | ≤1.6 | 2.2 a 2.6 | * Sterile | * As per |
| Method | SN | SN | SN | SN | SN | SN | Inminiz./Des. | Inminiz./Des. | Potentiometric | UV | Degree | | |
| Technique | CMI.T C.007 | CMI.T C.005 | CMI.T C.002 | CMI.T C.003 | CMI.T C.004 | CMI.T C.005 | CMI.T C.008 | CMI.T C.008 | CFQ.T C.035 | CFQ.T C.030 | CFQ.T C.003 | CMI.T C.017 | CMI.T C.018 |
| Base | <1.25 | 3.5 | >25 | 5 | 8 | >5 | 100 | 100 | 7.3 | 0.8 | 3.2 | OK | OK |
| A | <1.25 | 3.5-6 | 20-25 | >8 | 1-2.5 | 1.3-2.5 | 100 | 100 | 7.8 | 0.5 | ND | OK | OK |
| B | <1.25 | 1 | 5-10 | >8 | 2.5 | 1 | 100 | 100 | 8.1 | 0.4 | ND | OK | OK |
| C | <1.25 | 1-2 | 15-20 | >8 | 2.5-4 | 1.3-2.5 | 100 | 87.5 | 8.3 | 0.4 | ND | OK | OK |
| D | <1.25 | 3.5 | 15 | >8 | 1-2.5 | 1.25 | 100 | 100 | 8.5 | 0.4 | ND | OK | OK |
| E | <1.25 | 6 | 20 | 5 | 4 | >5 | 100 | 100 | 7.3 | 1.2 | 0 | OK | OK |

Safety was good for guinea pigs, mice, and rabbits, and, as indicated in Table 10, efficacy was good, particularly with formulations that lacked aluminum hydroxide (see e.g. the *Novyi, Septicum* and *Sordellii* columns; comparing E vs. D). These results were quite surprising, as the expectation reasonably could have been that a combination of aluminum hydroxide and the new polymer adjuvant (Group E) would outperform the new polymer-only formulation (Group D).

Example 4—PAA Supports a Protective Response in Canine when Formulated with Classical Inactivated or Recombinant Vaccines Inactivated Rabies Study.

Figure 8:
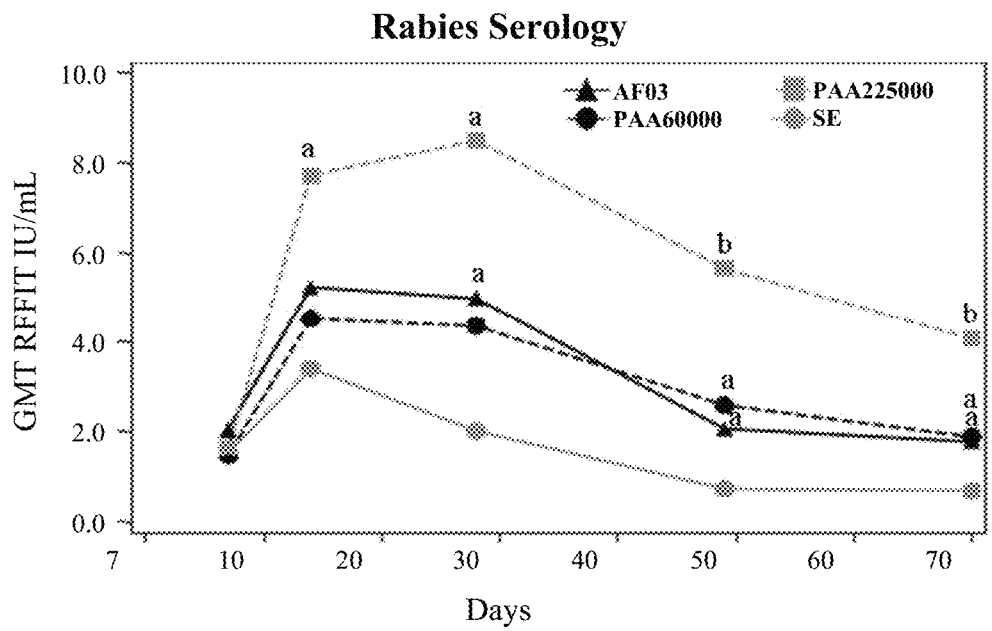
FIG. 8 is a graph presenting the rabies serology for canine groups vaccinated with inactivated rabies+PAA225000; AF03; PAA60000; or Squalene Emulsion.

Vaccines were prepared according to Table 11, and the results are presented in FIG. 8. All adjuvants tested appear to be safe for use in dogs, and all adjuvants induced seroconversion by Day 7, with positive titers were maintained up to 70 days following vaccination. PAA 225000 was the most effective adjuvant for improving inactivated rabies short term immunogenicity.

TABLE 11

Inactivated rabies vaccine formulations (Merial's IMRAB ® plus different adjuvants)

| Groups (6/grp) | Antigen 1 x SC (amount per dose) | Adjuvant (amount per dose) |
|---|---|---|
| A | Inactivated Rabies | PAA225000 (4 mg/ml) |
| B | (Rabies Glycoprotein | PAA60000 (4 mg/ml) |
| C | 5.6 μg/ml) | *AF03 (2.5%) |
| D | | **Squalene emulsion (SE) (2%) |

Figure 9:
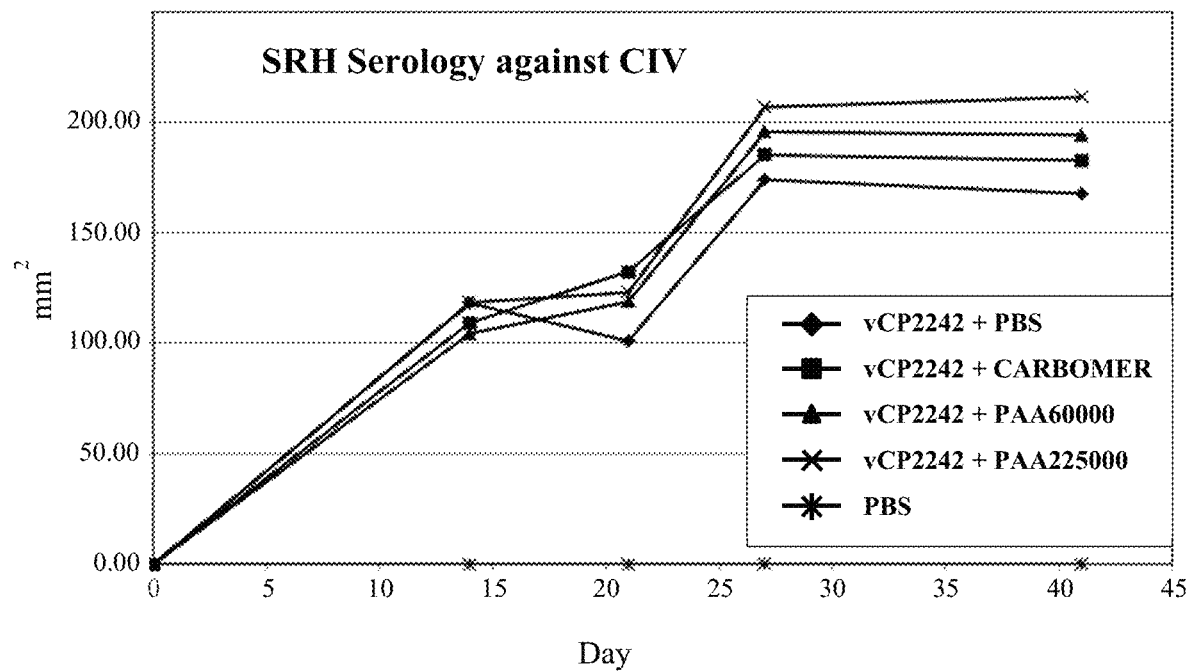
FIG. 9 is a graph presenting the CIV serology for canine groups vaccinated with canarypox-vectored recombinant influenza+(1) PBS; (2) CARBOMER (4 mg/ml); (3) PAA60000 (4 mg/ml); or (4) PAA225000 (4 mg/ml). Group 5 received only PBS (i.e. neither recombinant flu antigen nor adjuvant)
Figure 10:
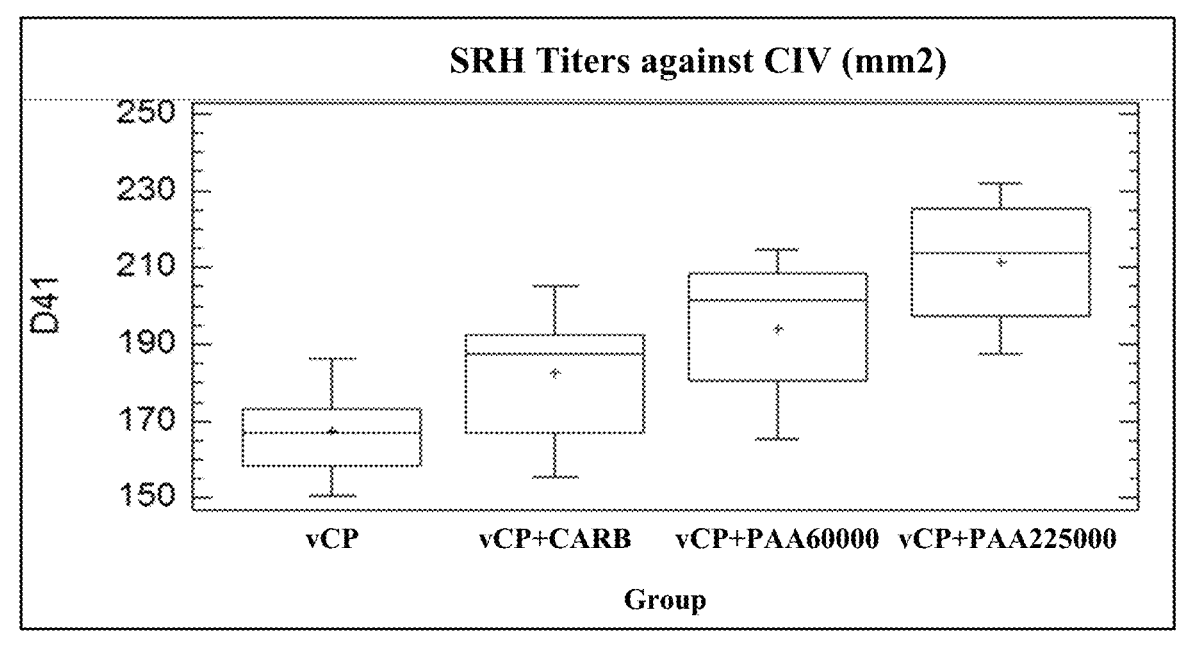

*AF03 is an alternative squalene emulsion-based adjuvant, produced using phase inversion (see J. Pharm. Sciences, Vol 101, Issue 12, 2012, and herein incorporated by reference in its entirety).
**Squalene emulsion is prepared using high pressure homogenization to form an oil-in-water emulsion Canarypox-vectored influenza study. Canarypox-vectored influenza vaccine formulations were prepared and tested on 5 groups, each containing 7 dogs (Table 12), and the results are presented in FIG. 10. High levels of IFNγ-producing cells were detected in all groups at D14, D27 and D41. Similar to the trend observed for the classical inactivated vaccine formulation above, the canarypox-vectored influenza antigens appear to be better adjuvanted by the higher MW PAA (i.e. PAA225000). vCP2242 is fully described and enabled by U.S. Pat. No. 7,425,336 (to Merial), and herein incorporated by reference in its entirety. But briefly here, vCP2242 is a recombinant ALVAC containing a codon-optimized HA gene from an H3N8 equine influenza virus (EIV), wherein the HA gene is inserted at the ALVAC C5 loci. Applicants assert that the results disclosed herein support the general conclusion that recombinant canarypox vectors are compatible with—and are well-adjuvanted by— the non-crosslinked PAA of the instant disclosure (see e.g. FIG. 9).

TABLE 12

Canarypox-vectored canine influenza vaccine formulations

| Groups (7/grp) | Antigen SC D 0 & D 21 (per dose) | Adjuvant (amount per dose) |
|---|---|---|
| 1 | vCP2242 titer 5.73 | PBS |
| 2 | $\log_{10} TCIC_{50}$ | CARBOMER (4 mg/ml) |
| 3 | | PAA60000 (4 mg/ml) |
| 4 | | PAA225000 (4 mg/ml) |
| 5 | PBS | |

Example 5—Non-Crosslinked PAA is an Effective Adjuvant for Equine Vaccines

Canarypox-Vectored Equine Influenza+Tetanus Toxin Study.

Figure 11:
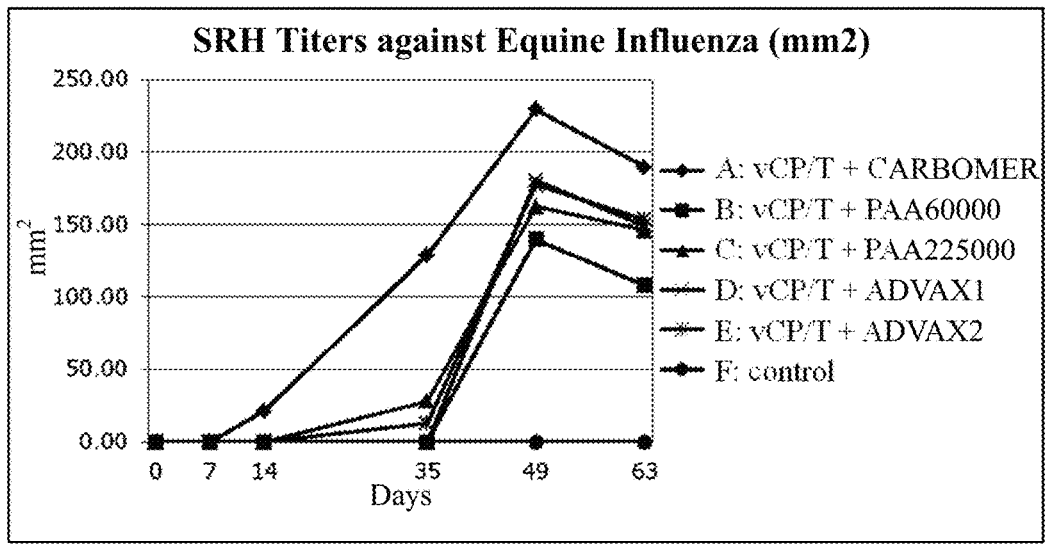
FIG. 11 is a graph showing the mean SRH-determined influenza antibody titer for equine groups vaccinated with vCP1533+vCP2242 (each harboring an HA gene from influenza virus) & tetanus toxin one of the following: (A) CARBOMER (4 mg/mL); (B) PAA60000 (4 mg/mL); (C) PAA225000 (4 mg/mL); (D) ADVAX1 (20 mg/mL); (E) ADVAX2 (20 mg/mL). Group (F) received only PBS (i.e. neither antigen nor adjuvant)
Figure 12:
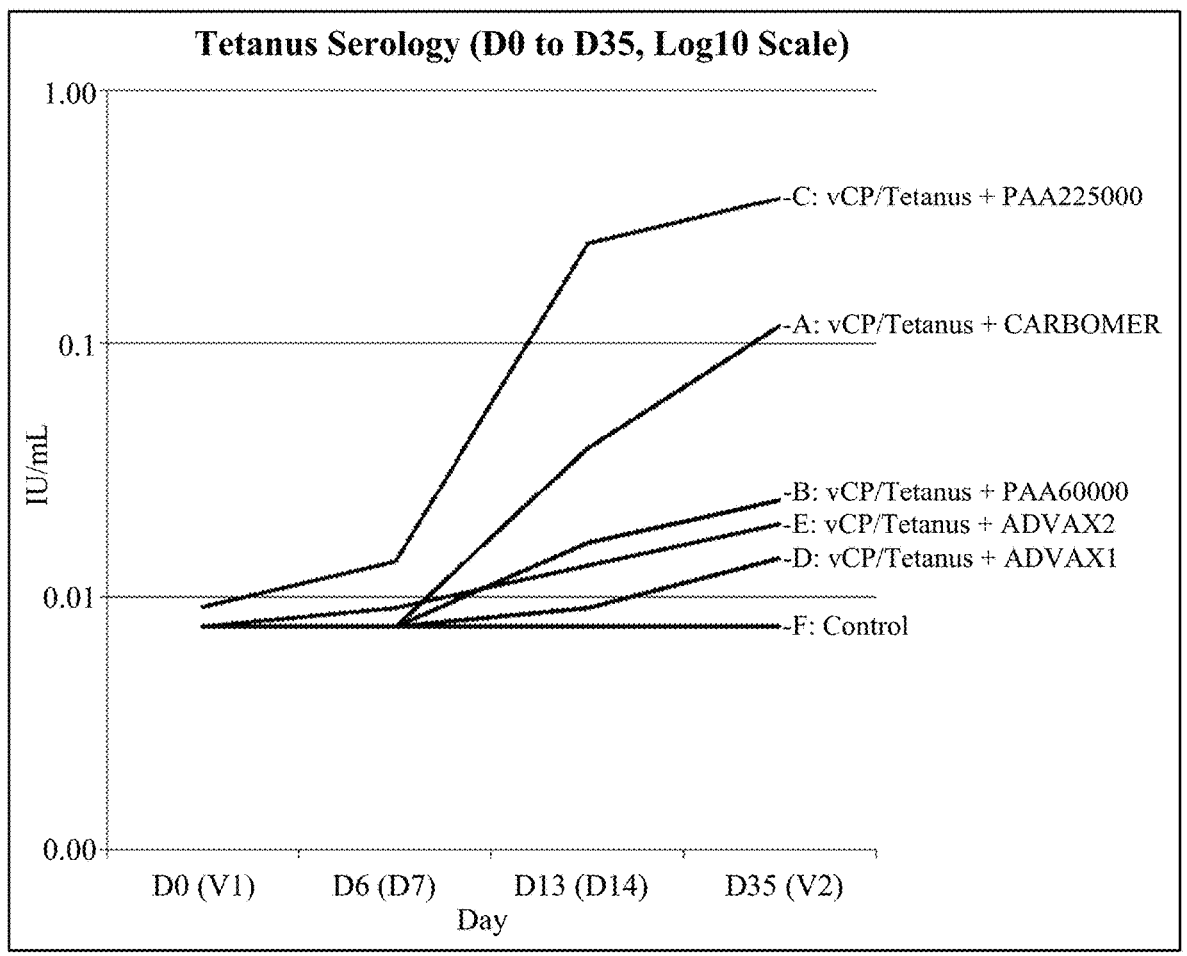
FIG. 12 is a graph showing the tetanus serology for each equine group to D35. Groups: same as depicted in FIG. 11.
Figure 13:
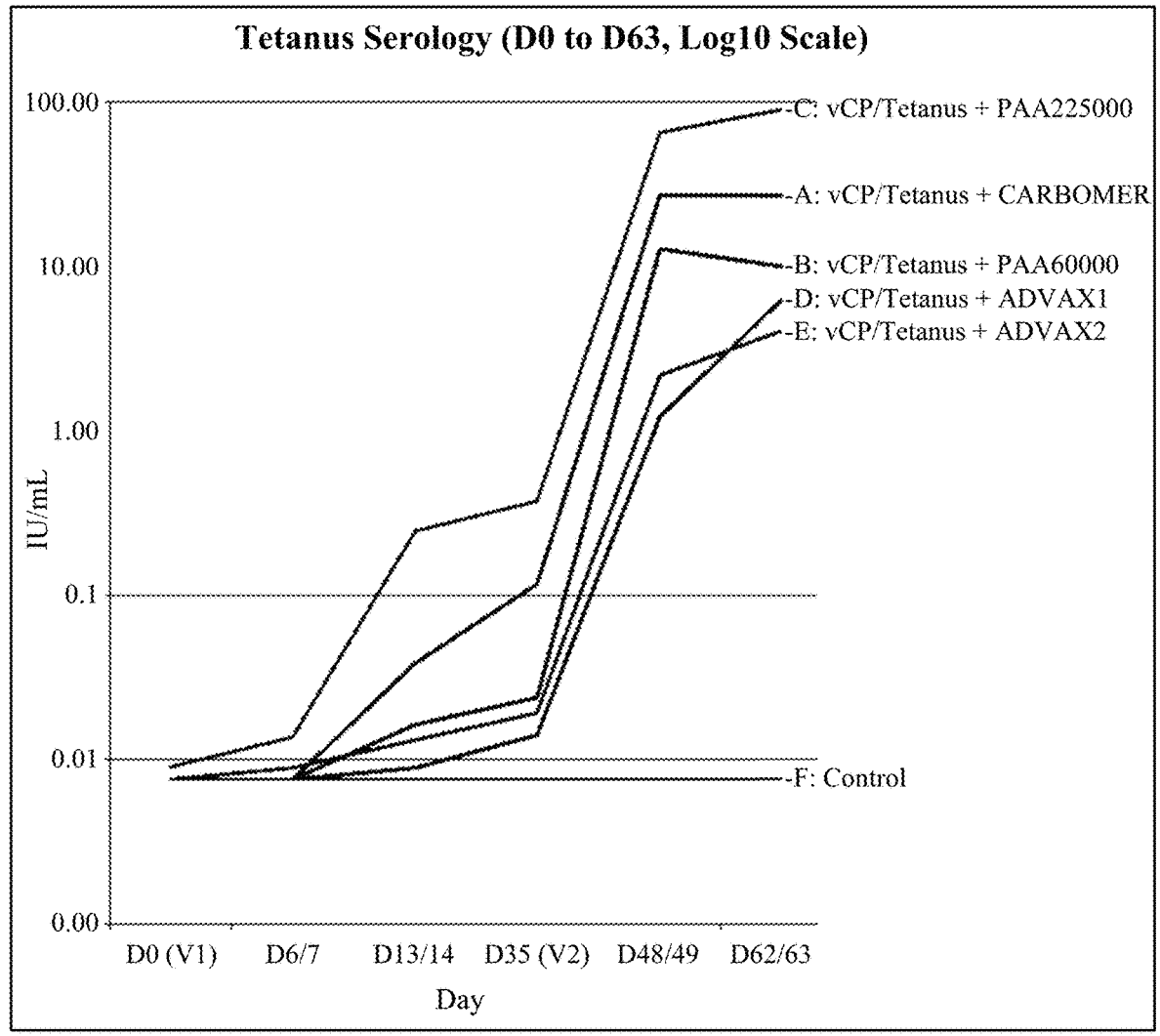
FIG. 13 is a graph showing the equine tetanus serology results out to D63.
Figure 14:
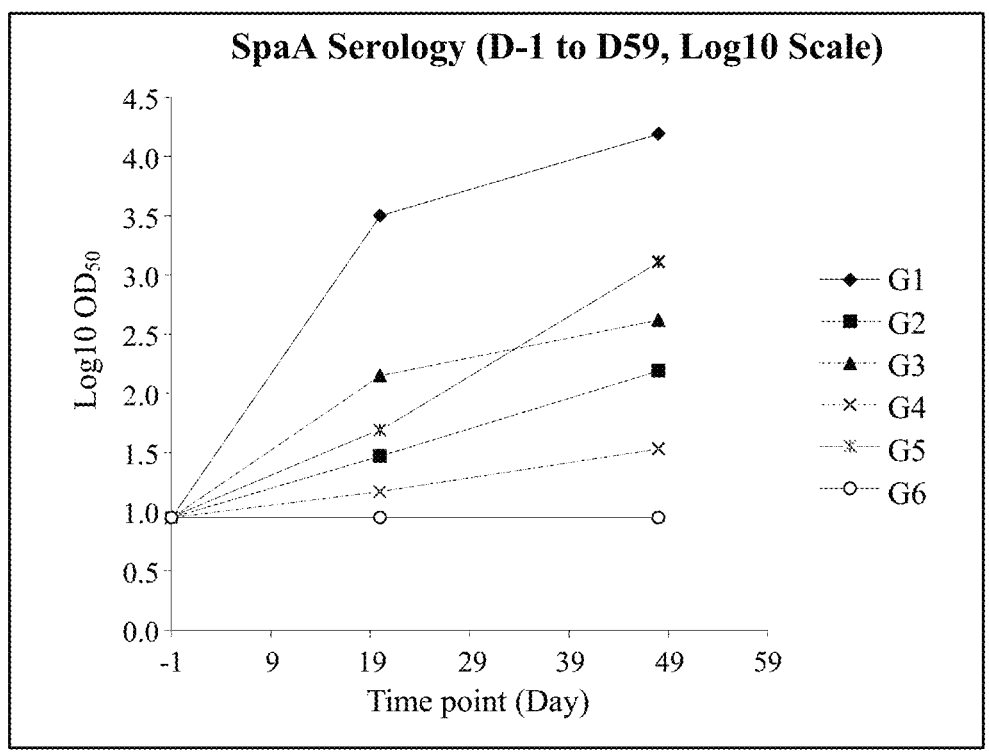
FIG. 14 is a graph showing the mean SpaA serology for each porcine group (to D59). Groups: (G1) SpaA+TS6; (G2) SpaA+PAA60000; (G3) SpaA+PAA225000; SpaA-FlaB-His+PBS; (G5) SpaA-FlaB-His+PAA225000; (G6) PBS.

Equines were administered the formulations according to Table 13. As indicated below, and in FIGS. 11-13, PAA strongly adjuvants two unrelated antigens to elicit in equines a protective immunological response.

TABLE 13

Canarypox-vectored equine influenza vaccine + tetanus formulations

| Group | Vaccination D 0 and D 35, 1 mL, IM (neck) Antigen | Adjuvant | Clinical monitoring** | Blood sampling |
|---|---|---|---|---|
| A (n = 8) | vCP1533 and vCP2242: | Carbomer (4 mg/mL) | D 0*, D 0 + 5/6 h, D 1, | D 0*, D 6/7, D 13/14 |
| B (n = 8) | 6.3 $\log_{10}$ FAID$_{50}$/mL | PAA60000 (4 mg/mL) | D 2, D 3 and D 35*, D 35 + | and D 35*, D 48/49, |
| C (n = 8) | (each) + Tetanus Toxin | PAA225000 (4 mg/mL) | 5/6 h, D 36, D 37, D 38 | D 62/63 |
| D (n = 8) | (100 Lf/mL) | ADVAX1 (20 mg/mL) | | |

TABLE 13-continued

Canarypox-vectored equine influenza vaccine + tetanus formulations

| Group | Antigen | Vaccination D 0 and D 35, 1 mL, IM (neck) Adjuvant | Clinical monitoring** | Blood sampling |
|---|---|---|---|---|
| E (n = 8) | | ADVAX2 (20 mg/mL) | | |
| F (n = 2) | N/A | N/A | D 0 and D 35 | |

ADVAX ™ adjuvants are derived from inulin (Vaccine. 2012 Aug. 3; 30(36): 5373-81; see also US 2014/0314739, to Vaxine Pty Ltd.). ADVAX1 is a preservative-free sterile suspension of delta inulin microparticles at 20 mg/ml in a bicarbonate buffer, whereas ADVAX2 additionally includes 10 µg CpG dinucleotide per 1 mg delta inulin.

Results.

By D14, all PAA225000 animals had protective titers >0.05 IU/ml. On D14, 6 of 8 animals from the carbomer-adjuvanted vaccine group were still <0.05 IU/ml. Accordingly, the PAA225000-adjuvanted vaccine formulation produced a significantly better seroconversion than did the carbomer-adjuvanted immunological formulation. By D49 (after the second vaccination), titers in the PAA225000 group were significantly and effectively high in all animals.

Example 6—PAA is an Effective Adjuvant for Porcine Vaccines

"SpaA" antigen porcine study. "SpaA" is intended to mean the "surface protective antigen" of *Erysipelothrix rhusiopathiae*, which is a pathogen that infects porcines and other animals, including canines. *Erysipelothrix rhusiopathiae* is a Gram-positive, catalase-negative, rod-shaped, non-spore-forming, non-acid-fast, non-motile bacterium. In pigs, *E. rhusiopathiae* causes "diamond skin disease." "TS6" means an oil-in-water emulsion described in, for example, U.S. Pat. No. 7,371,395 (to Merial). TS6 is formulated by adding about one (1) part of an antigen-containing aqueous component to about two (2) parts of an oily component, and then emulsifying the two components to form the final emulsion.

TABLE 14

Group and treatment definitions

| Group | Number | Treatment |
|---|---|---|
| G1 | 7 | SpaA antigen (150[1] µg/dose) + TS6 |
| G2 | 7 | SpaA antigen (100 µg/dose) + PAA60000 |
| G3 | 7 | SpaA antigen (100 µg/dose) + PAA225000 |
| G4 | 7 | SpaA-FlaB-His antigen (196[2] µg/dose) + PBS |
| G5 | 7 | SpaA-FlaB-His antigen (196[2] µg/dose) + PAA225000 |
| G6 | 7 | PBS |

[1]150 µg of SpaA in 2/3 treatment volume (tt) means 100 µg SpaA by 1/1 volume of tt.
[1]196 µg of the SpaA fusion protein is equivalent to 100 µg of the solitary SpaA protein. Accordingly, the effective amount of SpaA delivered to each Group was 100 µg.

While G1 produced the best results, it is notable that much of the dose volume for oil-in-water emulsions is taken up by the non-antigen components (as above, there is a 2:1 ratio of oily components to aqueous antigen components).

The invention will now be summarized by the following numbered paragraphs:

1. A pharmaceutically acceptable salt of a linear or branched polyacrylic acid polymer, for its use as an adjuvant in a vaccine composition, characterized in that said polyacrylic acid polymer salt has a weight average molecular weight Mw in the range of 350 to 650 kDa.

2. A pharmaceutically acceptable salt of a linear or branched polyacrylic acid polymer, for its use according to paragraph 1, characterized in that said polyacrylic acid polymer salt is exclusively composed of units corresponding to a salt of acrylic acid or is exclusively composed of units corresponding to the free acid form of acrylic acid and of units corresponding to a salt of acrylic acid.

3. A pharmaceutically acceptable salt of a linear or branched polyacrylic acid polymer, for its use according to paragraph 1 or 2, characterized in that it comprises less than 0.005% w/w of oxidizing agents, based on the total dry weight of said polyacrylic acid polymer salt.

4. A pharmaceutically acceptable salt of a linear or branched polyacrylic acid polymer, for its use according to any of the preceding paragraphs, characterized in that it comprises less than 0.001% w/w of oxidizing agents, based on the total dry weight of said polyacrylic acid polymer salt.

5. A pharmaceutically acceptable salt of a linear or branched polyacrylic acid polymer, for its use according to any one paragraphs 1 to 3, characterized in that it comprises less than 0.005% w/w of persulfates, based on the total dry weight of said polyacrylic acid polymer salt.

6. A pharmaceutically acceptable salt of a linear or branched polyacrylic acid polymer, for its use according to any of the preceding paragraphs, characterized in that it comprises less than 0.001% w/w of persulfates, based on the total dry weight of said polyacrylic acid polymer salt.

7. A pharmaceutically acceptable salt of a linear or branched polyacrylic acid polymer, for its use according to any one of the preceding paragraphs, characterized in that said polyacrylic acid polymer is a salt with Na+.

8. A pharmaceutically acceptable salt of a linear or branched polyacrylic acid polymer, for its use according to any one of the preceding paragraphs, characterized in that said polyacrylic acid polymer salt has a polydispersity index below or equal to 4, preferably below or equal to 2.5.

9. A pharmaceutically acceptable salt of a linear or branched polyacrylic acid polymer, for its use according to any one of the preceding paragraphs, characterized in that said polyacrylic acid polymer salt has a weight average molecular weight Mw in the range of 380 to 620 kDa and a polydispersity index below or equal to 4; or has a weight average molecular weight Mw in the range of 400 to 600 kDa and a polydispersity index below or equal to 4; or has a weight average molecular weight Mw in the range of 380 to 620 kDa and a polydispersity index below or equal to 2.5; or has a weight average molecular weight Mw in the range of 400 to 600 kDa and a polydispersity index below or equal to 2.

10. A pharmaceutically acceptable salt of a linear or branched polyacrylic acid polymer, for its use according to any one of the preceding paragraphs, characterized in that said polyacrylic acid polymer salt has a Mark Houwink slope higher or equal to 0.7.

11. A pharmaceutically acceptable salt of a linear or branched polyacrylic acid polymer, for its use according to any one of the preceding paragraphs, characterized in that it comprises less than 0.005% w/w of acrylic acid monomer in free acid form or salt form, based on the total dry weight of said polyacrylic acid polymer salt.

12. A pharmaceutically acceptable salt of a linear or branched polyacrylic acid polymer, for its use according to any one of the preceding paragraphs, characterized in that it is in a liquid formulation which has a pH in the range of 5.5 to 8.0.

13. A pharmaceutically acceptable salt of a linear or branched polyacrylic acid polymer in salt form, for its use according to paragraph 10, characterized in that it is in a buffered aqueous solution, in particular with a phosphate buffer, or a TRIS, Hepes, histidine or citrate buffer.

14. A pharmaceutically acceptable salt of a linear or branched polyacrylic acid polymer, for its use according to any one of the preceding paragraphs, characterized in that it is diafiltered.

15. A pharmaceutically acceptable salt of a linear or branched polyacrylic acid polymer, for its use according to any one of the preceding paragraphs, characterized in that it is sterilized.

16. A pharmaceutically acceptable salt of a linear or branched polyacrylic acid polymer, for its use according to any one of the preceding paragraphs, characterized it is used for enhancing the Th1 immune response obtained with the vaccine composition.

17. A vaccine composition comprising at least one vaccine agent and a pharmaceutically acceptable salt of polyacrylic acid polymer according to anyone of paragraphs 1 to 16, as an adjuvant.

18. The vaccine composition according to paragraph 17, characterized in that it comprises per dose, from 0.1 to 8 mg of the pharmaceutically acceptable salt of the polyacrylic acid polymer, preferably from 0.1 to 4 mg, and more preferably from 0.1 to 2 mg.

19. The vaccine composition according to paragraph 17 or 18, characterized in that the at least one vaccine agent is an antigen or a vector, such as a viral vector or a nucleic acid, expressing an antigen.

20. The vaccine composition according to paragraphs 18, characterized in that the antigen is a bacterial antigen originating from *Clostridium tetani, Clostridium diphtheriae, Bordetella pertussis, Haemophilus influenzae* type B, *Streptococcus pneumoniae, Neisseria meningitidis, Shigella* sp, *Salmonella typhi, Staphylococcus aureus, Staphylococcus epidermidis, Mycobacterium tuberculosis, Chlamydia trachomatis* or *pneumoniae* or *Streptococcus* sp; or is a viral antigen originating from the hepatitis A, B or C virus, the influenza virus, the respiratory syncytial virus, the rhinovirus, the West Nile virus, the rabies virus, the poliovirus, the HIV virus, the dengue virus, the Japanese encephalitis virus, the yellow fever virus, the cytomegalovirus or the herpes virus; or is a parasitic antigen originating from *Plasmodium* sp., *leishmania* sp. or *schistosoma* sp.; or is a tumor antigen.

21. The vaccine composition according to any one of paragraphs 17 to 19 characterized in that the at least one vaccine agent is an antigen or a vector such as a recombinant virus or nucleic acid encoding an antigen, the said antigen being originated from *Staphylococcus aureus* or from the cytomegalovirus.

22. The vaccine composition according to any one of paragraphs 17 to 21 characterized in that it is in a liquid form having a pH in the range of 6.0 to 8.0.

23. The vaccine composition according to paragraph 21 characterized in that it is in a buffered aqueous solution, in particular with a phosphate buffer or in a TRIS, Hepes, histidine or citrate buffer.

24. The vaccine composition according to any one of paragraphs 17 to 23 for its use in raising an immune response in an individual, in particular in a human being, with enhancement of the obtained Th1 immune response and/or with a balance between the obtained Th1 and Th2 immune responses.

25. A process for the preparation of a pharmaceutically acceptable salt of a polyacrylic acid polymer according to anyone of paragraphs 1 to 116 comprising the following successive steps:

a) having a solution of a polyacrylic acid polymer,
b) purifying the solution of the polyacrylic acid polymer, in order to eliminate impurities, and
c) sterilizing the purified solution of the polyacrylic acid polymer.

26. A preparation process, according to paragraph 25, characterized in that the polyacrylic acid polymer of the solution of step a) has a weight average molecular weight Mw in the range of 300 to 550 kDa.

27. A preparation process, according to paragraph 25 or 26, characterized in that the purification is carried out by dialysis, diafiltration, ultrafiltration or size exclusion chromatography.

28. A preparation process, according to paragraph 27, characterized in that the purification is carried out by diafiltration with a membrane of a cut off from 1 to 80 kDa, preferably to 2 to 50 kDa.

29. The preparation process, according to any one of paragraphs 25 to 28, characterized in that the purification is carried out in conditions allowing the obtaining of a polyacrylic acid polymer in solution having:
less than 0.005%, preferably less than 0.001% w/w of oxidizing agents, based on the total dry weight of said polyacrylic acid polymer obtained after purification, and/or less than 0.005%, preferably less than 0.001% w/w of persulfates, based on the total dry weight of said polyacrylic acid polymer obtained after purification,
less than 0.005% w/w of acrylic acid monomer in free acid form or salt form, based on the total dry weight of said polyacrylic acid polymer obtained after purification,
for the a polyacrylic acid polymer salt: a weight average molecular weight Mw in the range of 380 to 620 kDa and a polydispersity index below or equal to 4; or a weight average molecular weight Mw in the range of 400 to 600 kDa and a polydispersity index below or equal to 4; or a weight average molecular weight Mw in the range of 380 to 620 kDa and a polydispersity index below or equal to 2.5; or a weight average molecular weight Mw in the range of 400 to 600 kDa and a polydispersity index below or equal to 2.

30. The preparation process, according to any one of the paragraphs 25 to 29, characterized in that the sterilization is carried out in an autoclave.

31. The preparation process, according to any one of the paragraphs 25 to 30, characterized in that the purification and the sterilization are carried out on a solution of the pharmaceutically acceptable salt of the polyacrylic acid polymer.

32. The preparation process, according to any one of the paragraphs 25 to 31, characterized in that the purification is performed on a solution containing from 2 to 50 mg/mL of the pharmaceutically acceptable salt of the polyacrylic acid polymer.

33. A process for the storage of a solution of the polyacrylic acid polymer salt according to anyone of paragraphs 1 to 16 comprising the preparation process according to any one of the paragraphs 25 to 32, followed by a storage step of the obtained pharmaceutically acceptable salt of the polyacrylic acid polymer, in solution.

34. The storage process according to paragraph 33, characterized in that the storage step lasts at least 1 day and up to 2 years.

35. The storage process according to paragraph 33 or 34, characterized in that the storage step is carried out by placing the solution of the polyacrylic acid polymer salt in a container, at a temperature in a range of 0 to 30° C., preferably in the range of 2 to 8° C.

36. The storage process according to any one of paragraphs 33 to 35, characterized in that, during the storage, the solution of the polyacrylic acid polymer salt is kept away from light.

37. An immunological or vaccine composition comprising a therapeutically effective amount of an antigen component, a pharmaceutically or veterinarily acceptable carrier, and an adjuvant comprising or consisting essentially of a non-crosslinked polyacrylic acid (PAA) polymer having a Mw from about 350 kDa to about 650 kDa and a polydispersity index of less than about 4 or less than about 2.

38. The composition of paragraph 35, wherein the PAA has a Mw from about 400 kDa to about 600 kDa.

39. The composition of paragraph 36, wherein the PAA has a Mw from about 400 kDa to about 500 kDa.

40. The immunological or vaccine composition of paragraph 35, wherein the antigen component comprises an attenuated recombinant viral vector, a naturally or genetically-engineered live attenuated virus or microorganism, an inactivated virus or microorganism, a coccidian microorganism, a precocious coccidian microorganism, a proteinaceous subunit, a single-celled parasite, a multi-cellular parasite or any combination of the preceding.

41. The immunological or vaccine composition of paragraph 35, wherein the antigen component comprises: an *Eimeria* sp. or antigen thereof, *Escherichia coli* (*E. coli*) or antigen thereof, *Mycoplasma* hyopneumoniae (*M. hyo*), a bovine diarrhea virus (BDV) antigen, a recombinant canarypox vector containing and capable of in vivo expression of at least one protective immunogen, an inactivated full-length rabies glycoprotein, an *Erysipelothrix* sp., *Erysipelothrix rhusiopathiae*, a surface protective antigen (SpaA) from *E. rhusiopathiae*, a SpaA fusion protein comprising at least a portion of at least one additional immunogen, a SpaA-FlaB fusion protein, a SpaA-FlaB-His fusion protein, a *Clostridium* (*C.*) *perfringens* B/C toxin, a *C. perfringens* D toxin, *C. septicum* toxin, *C. novyi* toxin, a *C. tetani* toxin or any combination of the preceding.

42. The immunological or vaccine composition of paragraph 39, wherein the antigen component comprises or consists of an inactivated full-length rabies glycoprotein 43. The immunological or vaccine composition of paragraph 39, wherein the antigen component comprises or consists of a *C. perfringens* B/C toxin, a *C. perfringens* D toxin, *C. septicum* toxin, *C. novyi* toxin, a *C. tetani* toxin or combinations thereof.

44. The immunological or vaccine composition of paragraph 39, wherein the antigen component comprises *C. perfringens* B/C toxin, a *C. perfringens* D toxin, *C. septicum* toxin, *C. novyi* toxin and a *C. tetani* toxin.

45. The immunological or vaccine composition of paragraph 39, wherein the antigen component comprises a SpaA antigen or a fusion protein comprising the SpaA antigen.

46. The immunological or vaccine composition of paragraph 39, wherein the antigen component comprises an attenuated avipox virus or a DNA plasmid containing and capable of in vivo expression of an influenza gene.

47. The immunological or vaccine composition of paragraph 39, wherein the antigen component comprises an attenuated avipox virus or a DNA plasmid containing and capable of in vivo expression of a rabies glycoprotein gene.

48. A method of treating a bovine against infection caused by bacteria comprising administering to the bovine animal the vaccine composition of paragraph 41.

49. A method of treating a canine or equine against infection caused by influenza comprising administering to the canine or equine the vaccine composition of paragraph 44.

50. A method of treating a canine against infection caused by rabies virus comprising administering to the canine the vaccine composition of paragraph 44.

51. An avian coccidiosis vaccine, for in ovo administration, which comprises:
(a) an adjuvant that comprises non-crosslinked PAA having an average Mw from about 350 kDa to about 650 kDa; and
(b) a protozoan antigen selected from (1) one or more recombinantly expressed proteins; (2) one or more proteins or other macromolecules isolated from said protozoan by conventional means; (3) whole cell extracts or preparations from said protozoan; and (4) inactivated, live or live-precocious coccidians selected from: *Eimeria* (*E.*) *acervulina*, *E. adenoeides*, *E. brunetti*, *E. colchici*, *E. curvata*, *E. dispersa*, *E. duodenalis*, *E. fraterculae*, *E. gallopavonis*, *E. innocua*, *E. praecox*, *E. maxima*, *E. meleagridis*, *E. meleagrimitis*, *E. mitis*, *E. necatrix*, *E. phasiani*, *E. procera*, *E. tenella* and combinations thereof.

52. A method of treating a bovine against infection caused by *E. coli* or *M. hyo* comprising administering to the bovine the vaccine composition of paragraph 39, wherein the antigen component comprises *E. coli* or *M. hyo*.

53. The immunological or vaccine composition of paragraph 39, wherein the antigen component comprises *M. hyo*.

54. A method of treating a swine against infection caused by *M. hyo* comprising administering to the swine the vaccine composition of paragraph 51.

55. The immunological or vaccine composition of paragraph 39, wherein the antigen component comprises FIV.

56. A method of treating a feline against infection caused by FIV comprising administering to the feline the vaccine composition of paragraph 53.

57. The vaccine composition of paragraph 39, wherein the antigen component comprises a cancer antigen.

58. A method of treating a subject against cancer comprising administering to the subject the vaccine composition of paragraph 55.

59. The immunological or vaccine composition of paragraph 39, wherein the antigen component comprises canine coronavirus (CCV).

60. A method of treating a canine against infection caused by CCV comprising administering to the canine the vaccine composition of paragraph 57.

61. The immunological or vaccine composition of paragraph 39, wherein the antigen component comprises bovine rotavirus.

62. A method of treating a bovine against infection caused by bovine rotavirus comprising administering to the bovine the vaccine composition of paragraph 59.

63. The immunological or vaccine composition of paragraph 39, wherein the antigen component comprises canine influenza virus (CIV).

64. A method of treating a canine against infection caused by CIV comprising administering to the canine the vaccine composition of paragraph 61.

As disclosed herein, Applicants have discovered for the first time that certain molecular weight ranges of non-crosslinked (i.e. linear and branched) polyacrylic acid (PAA) polymer are particularly well-suited for adjuvanting the effect of immunogenic antigens, as well as for eliciting immunological responses independent of the antigens.

Importantly, Applicants have surprisingly found that these non-crosslinked PAA adjuvants were broadly useful across many different antigen types: an attenuated recombinant viral vector; a classically inactivated rabies glycoprotein; a SpaA peptide subunit; and bacterial toxins. Moreover, the disclosed PAA adjuvants functioned well across multiple animal types. Accordingly, Applicants submit that the disclosed non-crosslinked PAAs represent a novel and inventive "universal adjuvant."

What is claimed:

1. A vaccine adjuvant comprising a 20-80 kDa cut-off diafiltered pharmaceutically acceptable salt of a linear or branched polyacrylic acid polymer, wherein the polyacrylic acid polymer salt has a weight average molecular weight Mw in the range of 350 to 650 kDa; and a polydispersity index below or equal to 4; wherein the polyacrylic acid polymer salt comprises less than 0.005% w/w of oxidizing agents, based on the total dry weight of the polyacrylic acid polymer salt, and wherein the polyacrylic acid polymer salt is exclusively composed of acrylic acid units that are a salt of acrylic acid or is exclusively composed of acrylic acid units that are the free acid form of acrylic acid and of acrylic acid units that are a salt of acrylic acid.

2. The vaccine adjuvant of claim 1, wherein the polyacrylic acid polymer salt has a polydispersity index below or equal to 2.5; wherein the polyacrylic acid polymer salt has a weight average molecular weight Mw in the range of 380 to 620 kDa and a polydispersity index below or equal to 4; or has a weight average molecular weight Mw in the range of 400 to 600 kDa and a polydispersity index below or equal to 4; or has a weight average molecular weight Mw in the range of 380 to 620 kDa and a polydispersity index below or equal to 2.5; or has a weight average molecular weight Mw in the range of 400 to 600 kDa and a polydispersity index below or equal to 2.

3. The vaccine adjuvant of claim 1, wherein the polyacrylic acid polymer salt has a Mark Houwink slope higher or equal to 0.7.

4. The vaccine adjuvant of claim 1, formulated in a buffered aqueous solution selected from a phosphate, TRIS, Hepes, histidine, or citrate buffer.

5. The vaccine adjuvant of claim 1, which is sterilized.

6. The vaccine adjuvant of claim 1, wherein the polyacrylic acid polymer salt is capable of enhancing the Th1 immune response obtained with a vaccine composition.

7. A vaccine composition comprising at least one vaccine agent and the vaccine adjuvant of claim 1.

8. The vaccine composition of claim 7, comprising per dose, from about 0.1 to about 8 mg of the vaccine adjuvant, or from about 0.1 to about 4 mg, or from about 0.1 to 2 mg.

9. The vaccine composition of claim 7, wherein the at least one vaccine agent is an antigen or a vector capable of in vivo expression of an antigen; and/or wherein the antigen is a bacterial antigen of *Clostridium tetani*, *Clostridium diphtheriae*, *Bordetella pertussis*, *Haemophilus influenzae* type B, *Streptococcus pneumoniae*, *Neisseria meningitidis*, *Shigella* sp, *Salmonella typhi*, *Staphylococcus aureus*, *Staphylococcus epidermidis*, *Mycobacterium tuberculosis*, *Chlamydia trachomatis* or *pneumoniae* or *Streptococcus* sp; or is a viral antigen of the hepatitis A, B or C virus, the influenza virus, the respiratory syncytial virus, the rhinovirus, the West Nile virus, the rabies virus, the poliovirus, the HIV virus, the dengue virus, the Japanese encephalitis virus, the yellow fever virus, the cytomegalovirus or the herpes virus; or is a parasitic antigen of *Plasmodium* sp., *Leishmania* sp. or *Schistosoma* sp.; or is a tumor antigen.

10. The vaccine composition of claim 7, wherein the at least one vaccine agent is an antigen or a vector being originated from *Staphylococcus aureus* or from the cytomegalovirus.

11. The vaccine composition of claim 7, which is capable of raising an immune response in an animal or human, with enhancement of the obtained Th1 immune response and/or with a balance between the obtained Th1 and Th2 immune responses.

12. The vaccine adjuvant of claim 4, wherein the buffered aqueous solution has a pH in a range of 5.5 to 8.8.

13. The vaccine adjuvant of claim 1, wherein the pharmaceutically acceptable salt of a linear or branched polyacrylic acid polymer is a 20-50 kDa cut-off diafiltered pharmaceutically acceptable salt of a linear or branched polyacrylic acid polymer.

14. The vaccine adjuvant of claim 1, wherein the polyacrylic acid polymer salt comprises less than 0.001% w/w of oxidizing agents.

15. The vaccine adjuvant of claim 1, wherein the oxidizing agent is a persulfate.

16. The vaccine adjuvant of claim 1, wherein the polyacrylic acid polymer salt is a salt with $Na^+$.

* * * * *